United States Patent [19]

Sekiya et al.

[11] Patent Number: 5,332,833
[45] Date of Patent: Jul. 26, 1994

[54] β-OXO-β-BENZENEPROPANETHIOAMIDE COMPOUNDS

[75] Inventors: Tetsuo Sekiya; Mikio Tsutsui, both of Kanagawa; Tetsuro Shimpuku, Tokyo; Tatsuo Nagano, Tokyo; Junko Hayashi, Tokyo; Asami Seino, Kanagawa, all of Japan

[73] Assignee: Mitsubishi Kasei Corporation, Tokyo, Japan

[21] Appl. No.: 996,404

[22] Filed: Dec. 23, 1992

[30] Foreign Application Priority Data

Dec. 26, 1991 [JP] Japan .................................. 3-345657

[51] Int. Cl.$^5$ ................. C07C 327/38; C07C 327/48; C07D 233/96; A61K 31/165
[52] U.S. Cl. ............................... 548/338.5; 544/324; 544/335; 544/374; 546/293; 546/331; 548/325.5; 548/205; 548/235; 548/267.8; 548/559; 564/74; 564/78
[58] Field of Search ............... 548/338.5, 325.5, 267.8, 548/205, 235, 559; 564/74, 78; 514/599, 247, 269, 357, 365, 374, 383, 399, 427; 546/293, 331; 544/335, 374, 324

[56] References Cited

U.S. PATENT DOCUMENTS

| | | | |
|---|---|---|---|
| 4,028,409 | 6/1977 | Kramer et al. | 564/74 |
| 4,252,819 | 2/1981 | Hirata et al. | 548/338.5 |
| 4,299,845 | 11/1981 | Loebenberg et al. | 514/599 |
| 5,185,375 | 2/1993 | Cook et al. | 564/74 |

FOREIGN PATENT DOCUMENTS 0306440 3/1989 European Pat. Off. .
2183639 6/1987 United Kingdom ................. 564/74

OTHER PUBLICATIONS

Darré et al., Bulletin De La Societe Chimique De France No. 3-4 1975, pp. 829-834.
Barluenga et al., J. Chem. Soc. Perkins Trans. 1 1988 pp. 1739-1744.
Datta et al., Synthesis, No. 7 1988 pp. 556-557.
Okujima et al., Chemical Abstracts, vol. 116, 1992, p. 786 Abstract No. 83371j Abstracting JP 03 232853.
Yates et al., Tetrahedron, vol. 44, No. 11, pp. 3159-3170 (1988).

Primary Examiner—Floyd D. Higel
Attorney, Agent, or Firm—Wenderoth, Lind & Ponack

[57] ABSTRACT

The β-oxo-β-benzenepropanethioamide derivative of the present invention has potassium channel opening action and is useful for treatment of hypertension, asthma, hypersensitive colon syndrome, and enteritis through pharmacological actions including blood vessel dilation, bronchial tract dilation, relaxation of gastrointestinal tract smooth muscle, and the like. The present invention also includes a pharmaceutical composition containing, as the active ingredient, the compound of the present invention and a method for producing the same.

10 Claims, No Drawings

β-OXO-β-BENZENEPROPANETHIOAMIDE COMPOUNDS

FIELD OF THE INVENTION

The present invention relates to novel β-oxo-β-benzenepropanethioamide derivatives. More specifically, the present invention relates to novel β-oxo-β-benzenepropanethioamide derivatives and the pharmaceutically acceptable acid addition salts thereof, having potassium channel opening action and which are useful for treatment of hypertension, asthma, hypersensitive colon syndrome and enteritis through pharmacological actions including blood vessel dilation, bronchial tract dilation, relaxation of gastrointestinal tract smooth muscle, and the like.

BACKGROUND OF THE INVENTION

As β-oxo-β-benzenepropanethioamide derivatives, there have been known N, α,α-trimethyl-β-oxobenzenepropanethioamide (Compound of the following formula (A)) and N-phenyl-α,α-dimethyl-β-oxobenzenepropanethioamide (Compound of the following formula (B)) (Bull. Soc. Chim., Fr., 1975, 829), and as the α-monomethyl derivatives thereof, there have been known the N-propyl derivative (Compound of the following formula (C)) (Tetrahedron 44, 3159(19)), the N-phenyl derivative (Compounds of the following formulas (D) and (E)) (J. Chem. Soc. Perkin I, 1988, 1739) and 4-(2-methyl-3-oxo-3-phenyl-1-thioxopropyl) morpholine (Compound of the following formula (F)) (Synthesis 1988, 556), but none of the pharmaceutical actions thereof has been reported yet.

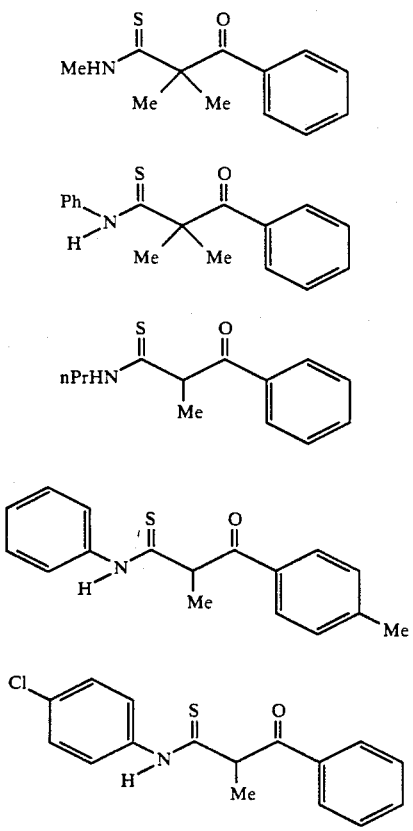

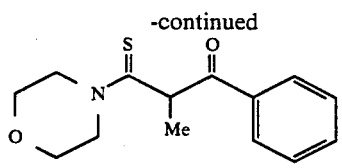

(In the above formulas, Me represents methyl group; nPr represents n-propyl group; and Ph represents phenyl group.)

Alternatively, a variety of compounds having antihypertensive action have been proposed, and it has been known, for example, that thioformamide derivatives having a heterocyclic ring such as pyridine and quinoline have an ability to lower the arterial pressure in spontaneous hypertensive rats (SHR) (see Japanese Patent Laid-open Nos. 130974/1980, 42687/1982, 7188/1984, 232281/1984, 211566/1989, 30875/1989, and 273/1990).

SUMMARY OF THE INVENTION

The present inventors have made investigations intensively based on these findings, and have found that the compounds of the present invention have potassium channel opening action. Thus, the inventors have achieved the present invention.

The gist of the present invention resides in β-oxo-β-benzenepropanethioamide derivatives represented by the following general formula (I):

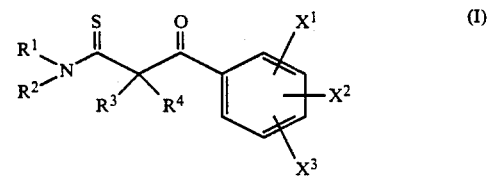

(in the above general formula (I), $R^1$ and $R^2$ independently represent hydrogen atom, an alkyl group of $C_1$ to $C_6$ or a cycloalkyl group of $C_3$ to $C_6$, or $R^1$ and $R^2$, when taken together, represent an alkylene group of $C_3$ to $C_6$; $R^3$ represents hydrogen atom, an alkyl group of $C_1$ to $C_6$ or a cycloalkyl group of $C_3$ to $C_6$; $R^4$ represents an alkyl group of $C_1$ to $C_6$ or a cycloalkyl group of $C_3$ to $C_6$; or $R^3$ and $R^4$, when taken together, represent an alkylene group of $C_2$ to $C_5$; $X^1$, $X^2$ and $X^3$ independently represent hydrogen atom, a halogen atom, an alkyl group of $C_1$ to $C_6$, a cycloalkyl group of $C_3$ to $C_6$, an alkoxy group of $C_1$ to $C_6$, trifluoromethyl group, cyano group, nitro group, a dialkylamino group of $C_2$ to $C_{12}$, sulfamoyl group, or a five-membered or six-membered heterocyclic group containing nitrogen atom as the hetero atom, which group may or may not have a substituent, except for the case that $R^1$ represents hydrogen atom; $R^2$ represents n-propyl group; $R^3$ represents hydrogen atom; $R^4$ represents methyl group; $X^1$, $X^2$ and $X^3$ represent hydrogen atom; and the case that $R^1$ represents hydrogen atom; $R^2$, $R^3$ and $R^4$ represent methyl group; and $X^1$, $X^2$ and $X^3$ represent hydrogen atom.)

The present invention also provides a pharmaceutical composition containing, as an active ingredient, a β-oxo-β-benzenepropanethioamide derivative of the above formula (I), an optical antipode thereof or a salt thereof.

The present invention also provides a process for the preparation of β-oxo-β-benzenepropanethioamide derivatives of the above formula (I), optical antipodes thereof or salts thereof.

DETAILED DESCRIPTION OF THE INVENTION

The present invention will now be explained in detail. The compounds of the present invention are β-oxo-β-benzenepropanethioamide derivatives represented by the following general formula (I):

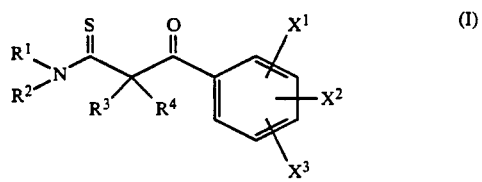

{in the above formula (I), $R^1$ and $R^2$ independently represent hydrogen atom, an alkyl group of $C_1$ to $C_6$ (methyl group, propyl group, hexyl group, etc.) or a cycloalkyl group of $C_3$ to $C_6$ (cyclopropyl group, cyclohexyl group, etc.), or $R^1$ and $R^2$, when taken together, represent an alkylene group of $C_3$ to $C_6$ (representing azetidine ring, hexamethyleneimine ring, etc. together with the nitrogen atom to which they are bonded); $R^3$ represents hydrogen atom, an alkyl group of $C_1$ to $C_6$ (methyl group, propyl group, hexyl group, etc.) or a cycloalkyl group of $C_3$ to $C_6$ (cyclopropyl group, cyclohexyl group, etc.); $R^4$ represents an alkyl group of $C_1$ to $C_6$ (methyl group, propyl group, hexyl group, etc.) or a cycloalkyl group of $C_3$ to $C_6$ (cyclopropyl group, cyclohexyl group, etc.); or $R^3$ and $R^4$, when taken together, represent an alkylene group of $C_2$ to $C_5$ (representing cyclopropane ring, cyclohexane ring, etc. together with the carbon atoms the which they are bonded); $X^1$, $X^2$ and $X^3$ independently represent hydrogen atom, a halogen atom (fluorine atom, chlorine atom, bromine atom, iodine atom, etc.), an alkyl group of $C_1$ to $C_6$ (methyl group, propyl group, hexyl group, etc.), a cycloalkyl group of $C_3$ to $C_6$ (cyclopropyl group, cyclohexyl group, etc. ), an alkoxy group of $C_1$ to $C_6$ (methoxy group, propoxy group, hexyloxy group), trifluoromethyl group, cyano group, nitro group, a dialkylamino group of $C_2$ to $C_{12}$ (dimethylamino group, diethylamino group, diisopropylamino group, etc.), sulfamoyl group, a five-membered or six-membered heterocyclic group containing nitrogen atom as the hetero atom (pyrrolyl group, imidazolyl group, pyrazolyl group, triazolyl group, thiazolyl group, oxazolyl group, pyridyl group, pyridazinyl group, pyridazinonyl group, pyrrolidonyl group, pyridonyl group, pyrimidinyl group, etc.), which group may or may not have a substituent [an alkyl group of $C_1$ to $C_6$ (methyl group, propyl group, hexyl group, etc.), an alkoxy group of $C_1$ to $C_6$ (methoxy group, propoxy group, hexyloxy group, etc.), a halogen atom (fluorine atom, chlorine atom, bromine atom, iodine atom, etc.), cyano group, phenyl group, an alkylthio group of $C_1$ to $C_6$ (methylthio group, propylthio group, hexylthio group, etc.), a haloalkyl group of $C_1$ to $C_6$ (methyl group, propyl group, hexyl group, etc., having one or more substituents selected from fluorine atom, chlorine atom, bromine atom, iodine atom, etc.)], except for the case that $R^1$ represents hydrogen atom; $R^2$ represents n-propyl group; $R^3$ represents hydrogen atom; $R^4$ represents methyl group; $X^1$, $X^2$ and $X^3$ represent hydrogen atom; and the case that $R^1$ represents hydrogen atom; $R^2$, $R^3$ and $R^4$ represent methyl group; and $X^1$, $X^2$ and $X^3$ represent hydrogen atom.)}, or the pharmaceutically acceptable acid addition salts thereof (salts of mineral acids such as hydrochloric acid, sulfuric acid, phosphoric acid, etc., or organic acids such as acetic acid, malonic acid, fumaric acid, maleic acid, methanesulfonic acid, p-toluenesulfonic acid, etc.)

Preferred examples of the compounds of the present invention include, among the above compounds, a compound wherein at least one of $X^1$, $X^2$ and $X^3$ represents a halogen atom, an alkyl group of $C_1$ to $C_6$, a cycloalkyl group of $C_3$ to $C_5$, an alkoxy group of $C_1$ to $C_6$, trifluoromethyl group, cyano group, nitro group, a dialkylamino group of $C_2$ to $C_{12}$, sulfamoyl group, a five-membered or six-membered heterocyclic group containing nitrogen atom as the hetero atom, which group may or may not have a substituent.

More preferred compounds include, among the above compounds, a compound wherein at least one of $X^1$, $X^2$ and $X^3$ represents a five-membered or six-membered heterocyclic group containing nitrogen atom as the hetero atom, which group may ormay not have a substituent.

As the five-membered or six-membered heterocyclic group, preference is given to pyrrolyl group, imidazolyl group, pyrazolyl grouop, triazolyl group, pyridyl group and pyridonyl group; in particular, imidazolyl group is preferable.

As the substituent on the heterocyclic ring, preference is given to an alkyl group of $C_1$ to $C_6$, a halogen atom, phenyl group and an alkylthio group; in particular, a halogen atom is preferable.

Specific examples of the compounds of the present invention are shown hereinbelow in Table 1.

TABLE 1

| Compound No. | $R^1$ | $R^2$ | $R^3$ | $R^4$ | $X^1$ | $X^2$ | $X^3$ |
|---|---|---|---|---|---|---|---|
| 1 | H | H | H | methyl | H | H | H |
| 2 | H | H | H | methyl | 2-(1-imidazolyl) | H | H |
| 3 | H | H | H | methyl | 3-(1-imidazolyl) | H | H |
| 4 | H | H | H | methyl | 4-(1-imidazolyl) | H | H |
| 5 | H | H | H | methyl | 4-fluoro | H | H |
| 6 | H | H | —CH$_2$CH$_2$CH$_2$— | | 4-(1-imidazolyl) | H | H |
| 7 | H | H | —CH$_2$CH$_2$CH$_2$— | | 4-(2-methyl-1-imidazolyl) | H | H |
| 8 | H | H | —CH$_2$CH$_2$CH$_2$— | | 4-(2-ethyl-1-imidazolyl) | H | H |
| 9 | H | H | —CH$_2$CH$_2$CH$_2$— | | 4-(2-isopropyl-1-imidazolyl) | H | H |
| 10 | H | H | —CH$_2$CH$_2$CH$_2$— | | 4-(2-propyl-1-imidazolyl) | H | H |
| 11 | H | H | —CH$_2$CH$_2$CH$_2$— | | 4(2-phenyl-1-imidazolyl) | H | H |
| 12 | H | H | —CH$_2$CH$_2$CH$_2$— | | 4-(2-iodo-1-imidazolyl) | H | H |
| 13 | H | H | —CH$_2$CH$_2$CH$_2$— | | 4-(2-methoxy-1-imidazolyl) | H | H |
| 14 | H | H | —CH$_2$CH$_2$CH$_2$— | | 4-(2-methylthio-1-imidazolyl) | H | H |
| 15 | H | H | —CH$_2$CH$_2$CH$_2$— | | 4-(2-cyano-1-imidazolyl) | H | H |

TABLE 1-continued

| Compound No. | R¹ | R² | R³ R⁴ | X¹ | X² | X³ |
|---|---|---|---|---|---|---|
| 16 | H | H | —CH₂CH₂CH₂— | 4-(2-chloro-1-imidazolyl) | H | H |
| 17 | H | H | —CH₂CH₂CH₂— | 4-(4-methyl-1-imidazolyl) | H | H |
| 18 | H | H | —CH₂CH₂CH₂— | 4-(4-methyl-1-imidazolyl) | H | H |
| 19 | H | H | —CH₂CH₂CH₂— | 4-(5-methyl-1-imidazolyl) | H | H |
| 20 | H | H | —CH₂CH₂CH₂— | 4-(2-fluoromethyl-1-imidazolyl) | H | H |
| 21 | H | H | —CH₂CH₂CH₂— | 4-(2-difluoromethyl-1-imidazolyl) | H | H |
| 22 | H | H | —CH₂CH₂CH₂— | 4-(2-trifluoromethyl-1-imidazolyl) | H | H |
| 23 | H | H | —CH₂CH₂CH₂— | 4-(4,5-dichloro-1-imidazolyl) | H | H |
| 24 | H | H | —CH₂CH₂CH₂— | 4-(1-imidazolyl) | 3-fluoro | H |
| 25 | H | H | —CH₂CH₂CH₂— | 4-(1-imidazolyl) | 3-chloro | H |
| 26 | H | H | —CH₂CH₂CH₂— | 4-(1-imidazolyl) | 3-bromo | H |
| 27 | H | H | —CH₂CH₂CH₂— | 4-(1-imidazolyl) | 3-iodo | H |
| 28 | H | H | —CH₂CH₂CH₂— | 4-(1-imidazolyl) | 3-cyano | H |
| 29 | H | H | —CH₂CH₂CH₂— | 4-(1-imidazolyl) | 3-methyl | H |
| 30 | H | H | —CH₂CH₂CH₂— | 4-(1-imidazolyl) | 3-ethyl | H |
| 31 | H | H | —CH₂CH₂CH₂— | 4-(1-imidazolyl) | 3-isopropyl | H |
| 32 | H | H | —CH₂CH₂CH₂— | 4-(1-imidazolyl) | 3-propyl | H |
| 33 | H | H | —CH₂CH₂CH₂— | 4-(1-imidazolyl) | 3-methoxy | H |
| 34 | H | H | —CH₂CH₂CH₂— | 4-(1-imidazolyl) | 3-ethoxy | H |
| 35 | H | H | —CH₂CH₂CH₂— | 4-(1-imidazolyl) | 3-isopropoxy | H |
| 36 | H | H | —CH₂CH₂CH₂— | 4-(1-imidazolyl) | 3-propoxy | H |
| 37 | H | H | —CH₂CH₂CH₂— | 4-(1-imidazolyl) | 3-trifluoromethyl | H |
| 38 | H | H | —CH₂CH₂CH₂— | 3-(1-imidazolyl) | H | H |
| 39 | H | H | —CH₂CH₂CH₂— | 3-(2-methyl-1-imidazolyl) | H | H |
| 40 | H | H | —CH₂CH₂CH₂— | 3-(2-ethyl-1-imidazolyl) | H | H |
| 41 | H | H | —CH₂CH₂CH₂— | 3-(2-isopropyl-1-imidazolyl) | H | H |
| 42 | H | H | —CH₂CH₂CH₂— | 3-(2-propyl-1-imidazolyl) | H | H |
| 43 | H | H | —CH₂CH₂CH₂— | 3-(2-phenyl-1-imidazolyl) | H | H |
| 44 | H | H | —CH₂CH₂CH₂— | 3-(2-iodo-1-imidazolyl) | H | H |
| 45 | H | H | —CH₂CH₂CH₂— | 3-(2-methoxy-1-imidazolyl) | H | H |
| 46 | H | H | —CH₂CH₂CH₂— | 3-(2-methylthio-1-imidazolyl) | H | H |
| 47 | H | H | —CH₂CH₂CH₂— | 3-(2-cyano-1-imidazolyl) | H | H |
| 48 | H | H | —CH₂CH₂CH₂— | 3-(2-chloro-1-imidazolyl) | H | H |
| 49 | H | H | —CH₂CH₂CH₂— | 3-(2-methyl-1-imidazolyl) | H | H |
| 50 | H | H | —CH₂CH₂CH₂— | 3-(4-methyl-1-imidazolyl) | H | H |
| 51 | H | H | —CH₂CH₂CH₂— | 3-(5-methyl-1-imidazolyl) | H | H |
| 52 | H | H | —CH₂CH₂CH₂— | 3-(2-fluoromethyl-1-imidazolyl) | H | H |
| 53 | H | H | —CH₂CH₂CH₂— | 3-(2-difluoromethyl-1-imidazolyl) | H | H |
| 54 | H | H | —CH₂CH₂CH₂— | 3-(2-trifluoromethyl-1-imidazolyl) | H | H |
| 55 | H | H | —CH₂CH₂CH₂— | 3-(4,5-dichloro-1-imidazolyl) | H | H |
| 56 | H | H | —CH₂CH₂CH₂— | 3-(1-imidazolyl) | 4-fluoro | H |
| 57 | H | H | —CH₂CH₂CH₂— | 3-(1-imidazolyl) | 4-chloro | H |
| 58 | H | H | —CH₂CH₂CH₂— | 3-(1-imidazolyl) | 4-bromo | H |
| 59 | H | H | —CH₂CH₂CH₂— | 3-(1-imidazolyl) | 4-iodo | H |
| 60 | H | H | —CH₂CH₂CH₂— | 3-(1-imidazolyl) | 4-cyano | H |
| 61 | H | H | —CH₂CH₂CH₂— | 3-(1-imidazolyl) | 4-methyl | H |
| 62 | H | H | —CH₂CH₂CH₂— | 3-(1-imidazolyl) | 4-ethyl | H |
| 63 | H | H | —CH₂CH₂CH₂— | 3-(1-imidazolyl) | 4-isopropyl | H |
| 64 | H | H | —CH₂CH₂CH₂— | 3-(1-imidazolyl) | 4-propyl | H |
| 65 | H | H | —CH₂CH₂CH₂— | 3-(1-imidazolyl) | 4-methoxy | H |
| 66 | H | H | —CH₂CH₂CH₂— | 3-(1-imidazolyl) | 4-ethoxy | H |
| 67 | H | H | —CH₂CH₂CH₂— | 3-(1-imidazolyl) | 4-isopropoxy | H |
| 68 | H | H | —CH₂CH₂CH₂— | 3-(1-imidazolyl) | 4-propoxy | H |
| 69 | H | H | —CH₂CH₂CH₂— | 3-(1-imidazolyl) | 4-trifluoromethyl | H |
| 70 | H | H | —CH₂CH₂CH₂— | 3-(1-imidazolyl) | H | H |
| 71 | H | H | —CH₂CH₂CH₂— | 3-(2-methoxy-1-imidazolyl) | H | H |
| 72 | H | H | —CH₂CH₂CH₂— | 3-(2-methylthio-1-imidazolyl) | H | H |
| 73 | H | H | —CH₂CH₂CH₂— | 2-(1-imidazolyl) | H | H |
| 74 | H | H | —CH₂CH₂CH₂— | 2-(2-methyl-1-imidazolyl) | H | H |
| 75 | H | H | —CH₂CH₂CH₂— | 2-(2-ethyl-1-imidazolyl) | H | H |
| 76 | H | H | —CH₂CH₂CH₂— | 2-(2-isopropyl-1-imidazolyl) | H | H |
| 77 | H | H | —CH₂CH₂CH₂— | 2-(2-propyl-1-imidazolyl) | H | H |
| 78 | H | H | —CH₂CH₂CH₂— | 2-(2-phenyl-1-imidazolyl) | H | H |
| 79 | H | H | —CH₂CH₂CH₂— | 2-(2-iodo-1-imidazolyl) | H | H |
| 80 | H | H | —CH₂CH₂CH₂— | 2-(2-methoxy-1-imidazolyl) | H | H |
| 81 | H | H | —CH₂CH₂CH₂— | 2-(2-methylthio-1-imidazolyl) | H | H |
| 82 | H | H | —CH₂CH₂CH₂— | 2-(2-cyano-1-imidazolyl) | H | H |
| 83 | H | H | —CH₂CH₂CH₂— | 2-(2-chloro-1-imidazolyl) | H | H |
| 84 | H | H | —CH₂CH₂CH₂— | 2-(2-metyl-1-imidazolyl) | H | H |
| 85 | H | H | —CH₂CH₂CH₂— | 2-(4-metyl-1-imidazolyl) | H | H |
| 86 | H | H | —CH₂CH₂CH₂— | 2-(5-metyl-1-imidazolyl) | H | H |
| 87 | H | H | —CH₂CH₂CH₂— | 2-(2-fluoromethyl-1-imidazolyl) | H | H |
| 88 | H | H | —CH₂CH₂CH₂— | 2-(2-difluoromethyl-1-imidazolyl) | H | H |
| 89 | H | H | —CH₂CH₂CH₂— | 2-(2-trifluoromethyl-1-imidazolyl) | H | H |
| 90 | H | H | —CH₂CH₂CH₂— | 2-(4,5-dichloro-1-imidazolyl) | H | H |
| 91 | H | H | —CH₂CH₂CH₂— | 2-(1-imidazolyl) | 3-fluoro | H |
| 92 | H | H | —CH₂CH₂CH₂— | 2-(1-imidazolyl) | 3-chloro | H |
| 93 | H | H | —CH₂CH₂CH₂— | 2-(1-imidazolyl) | 3-bromo | H |
| 94 | H | H | —CH₂CH₂CH₂— | 2-(1-imidazolyl) | 3-iodo | H |

TABLE 1-continued

| Compound No. | R¹ | R² | R³ | R⁴ | X¹ | X² | X³ |
|---|---|---|---|---|---|---|---|
| 95 | H | H | —CH₂CH₂CH₂— | | 2-(1-imidazolyl) | 3-cyano | H |
| 96 | H | H | —CH₂CH₂CH₂— | | 2-(1-imidazolyl) | 3-methyl | H |
| 97 | H | H | —CH₂CH₂CH₂— | | 2-(1-imidazolyl) | 3-ethyl | H |
| 98 | H | H | —CH₂CH₂CH₂— | | 2-(1-imidazolyl) | 3-isopropyl | H |
| 99 | H | H | —CH₂CH₂CH₂— | | 2-(1-imidazolyl) | 3-propyl | H |
| 100 | H | H | —CH₂CH₂CH₂— | | 2-(1-imidazolyl) | 3-methoxy | H |
| 101 | H | H | —CH₂CH₂CH₂— | | 2-(1-imidazolyl) | 3-ethoxy | H |
| 102 | H | H | —CH₂CH₂CH₂— | | 2-(1-imidazolyl) | 3-isopropoxy | H |
| 103 | H | H | —CH₂CH₂CH₂— | | 2-(1-imidazolyl) | 3-propoxy | H |
| 104 | H | H | —CH₂CH₂CH₂— | | 2-(1-imidazolyl) | 3-trifluoromethyl | H |
| 105 | H | H | methyl | methyl | H | H | H |
| 106 | H | H | methyl | methyl | 4-(1-imidazolyl) | H | H |
| 107 | H | H | methyl | methyl | 4-(2-methyl-1-imidazolyl) | H | H |
| 108 | H | H | methyl | methyl | 4-(2-ethyl-1-imidazolyl) | H | H |
| 109 | H | H | methyl | methyl | 4-(2-isopropyl-1-imidazolyl) | H | H |
| 110 | H | H | methyl | methyl | 4-(2-propyl-1-imidazolyl) | H | H |
| 111 | H | H | methyl | methyl | 4-(2-phenyl-1-imidazolyl) | H | H |
| 112 | H | H | methyl | methyl | 4-(2-iodo-1-imidazolyl) | H | H |
| 113 | H | H | methyl | methyl | 4-(2-methoxy-1-imidazolyl) | H | H |
| 114 | H | H | methyl | methyl | 4-(2-methylthio-1-imidazolyl) | H | H |
| 115 | H | H | methyl | methyl | 4-(2-cyano-1-imidazolyl) | H | H |
| 116 | H | H | methyl | methyl | 4-(2-chloro-1-imidazolyl) | H | H |
| 117 | H | H | methyl | methyl | 4-(2-methyl-1-imidazolyl) | H | H |
| 118 | H | H | methyl | methyl | 4-(4-methyl-1-imidazolyl) | H | H |
| 119 | H | H | methyl | methyl | 4-(5-methyl-1-imidazolyl) | H | H |
| 120 | H | H | methyl | methyl | 4-(2-fluoromethyl-1-imidazolyl) | H | H |
| 121 | H | H | methyl | methyl | 4-(2-difluoromethyl-1-imidazolyl) | H | H |
| 122 | H | H | methyl | methyl | 4-(2-trifluoromethyl-1-imidazolyl) | H | H |
| 123 | H | H | methyl | methyl | 4-(4,5-dichloro-1-imidazolyl) | H | H |
| 124 | H | H | methyl | methyl | 4-(1-imidazolyl) | 3-fluoro | H |
| 125 | H | H | methyl | methyl | 4-(1-imidazolyl) | 3-chloro | H |
| 126 | H | H | methyl | methyl | 4-(1-imidazolyl) | 3-bromo | H |
| 127 | H | H | methyl | methyl | 4-(1-imidazolyl) | 3-iodo | H |
| 128 | H | H | methyl | methyl | 4-(1-imidazolyl) | 3-cyano | H |
| 129 | H | H | methyl | methyl | 4-(1-imidazolyl) | 3-methy | H |
| 130 | H | H | methyl | methyl | 4-(1-imidazolyl) | 3-ethyl | H |
| 131 | H | H | methyl | methyl | 4-(1-imidazolyl) | 3-isopropyl | H |
| 132 | H | H | methyl | methyl | 4-(1-imidazolyl) | 3-propyl | H |
| 133 | H | H | methyl | methyl | 4-(1-imidazolyl) | 3-methoxy | H |
| 134 | H | H | methyl | methyl | 4-(1-imidazolyl) | 3-ethoxy | H |
| 135 | H | H | methyl | methyl | 4-(1-imidazolyl) | 3-isopropoxy | H |
| 136 | H | H | methyl | methyl | 4-(1-imidazolyl) | 3-propoxy | H |
| 137 | H | H | methyl | methyl | 4-(1-imidazolyl) | 3-trifluoromethyl | H |
| 138 | H | H | methyl | methyl | 3-(1-imidazolyl) | H | H |
| 139 | H | H | methyl | methyl | 3-(2-methyl-1-imidazolyl) | H | H |
| 140 | H | H | methyl | methyl | 3-(2-ethyl-1-imidazolyl) | H | H |
| 141 | H | H | methyl | methyl | 3-(2-isopropyl-1-imidazolyl) | H | H |
| 142 | H | H | methyl | methyl | 3-(2-propyl-1-imidazolyl) | H | H |
| 143 | H | H | methyl | methyl | 3-(2-phenyl-1-imidazolyl) | H | H |
| 144 | H | H | methyl | methyl | 3-(2-iodo-1-imidazolyl) | H | H |
| 145 | H | H | methyl | methyl | 3-(2-methoxy-1-imidazolyl) | H | H |
| 146 | H | H | methyl | methyl | 3-(2-methylthio-1-imidazolyl) | H | H |
| 147 | H | H | methyl | methyl | 3-(2-cyano-1-imidazolyl) | H | H |
| 148 | H | H | methyl | methyl | 3-(2-chloro-1-imidazolyl) | H | H |
| 149 | H | H | methyl | methyl | 3-(2-methyl-1-imidazolyl) | H | H |
| 150 | H | H | methyl | methyl | 3-(4-methyl-1-imidazolyl) | H | H |
| 151 | H | H | methyl | methyl | 3-(5-methyl-1-imidazolyl) | H | H |
| 152 | H | H | methyl | methyl | 3-(2-fluoromethyl-1-imidazolyl) | H | H |
| 153 | H | H | methyl | methyl | 3-(2-difluoromethyl-1-imidazolyl) | H | H |
| 154 | H | H | methyl | methyl | 3-(2-trifluoromethyl-1-imidazolyl) | H | H |
| 155 | H | H | methyl | methyl | 3-(4,5-dichloro-1-imidazolyl) | H | H |
| 156 | H | H | methyl | methyl | 3-(1-imidazolyl) | 4-fluoro | H |
| 157 | H | H | methyl | methyl | 3-(1-imidazolyl) | 4-chloro | H |
| 158 | H | H | methyl | methyl | 3-(1-imidazolyl) | 4-bromo | H |
| 159 | H | H | methyl | methyl | 3-(1-imidazolyl) | 4-iodo | H |
| 160 | H | H | methyl | methyl | 3-(1-imidazolyl) | 4-cyano | H |
| 161 | H | H | methyl | methyl | 3-(1-imidazolyl) | 4-methyl | H |
| 162 | H | H | methyl | methyl | 3-(1-imidazolyl) | 4-ethyl | H |
| 163 | H | H | methyl | methyl | 3-(1-imidazolyl) | 4-isopropyl | H |
| 164 | H | H | methyl | methyl | 3-(1-imidazolyl) | 4-propyl | H |
| 165 | H | H | methyl | methyl | 3-(1-imidazolyl) | 4-methoxy | H |
| 166 | H | H | methyl | methyl | 3-(1-imidazolyl) | 4-ethoxy | H |
| 167 | H | H | methyl | methyl | 3-(1-imidazolyl) | 4-isopropoxy | H |
| 168 | H | H | methyl | methyl | 3-(1-imidazolyl) | 4-propoxy | H |
| 169 | H | H | methyl | methyl | 3-(1-imidazolyl) | 4-trifluoromethyl | H |
| 170 | H | H | methyl | methyl | 3-(1-imidazolyl) | H | H |
| 171 | H | H | methyl | methyl | 3-(2-methoxy-1-imidazoly) | H | H |
| 172 | H | H | methyl | methyl | 3-(2-methythio-1-imidazolyl) | H | H |
| 173 | H | H | methyl | methyl | 2-(1-imidazolyl) | H | H |

TABLE 1-continued

| Compound No. | R¹ | R² | R³ | R⁴ | X¹ | X² | X³ |
|---|---|---|---|---|---|---|---|
| 174 | H | H | methyl | methyl | 2-(2-methyl-1-imidazolyl) | H | H |
| 175 | H | H | methyl | methyl | 2-(2-ethyl-1-imidazolyl) | H | H |
| 176 | H | H | methyl | methyl | 2-(2-isopropyl-1-imidazolyl) | H | H |
| 177 | H | H | methyl | methyl | 2-(2-propyl-1-imidazolyl) | H | H |
| 178 | H | H | methyl | methyl | 2-(2-phenyl-1-imidazolyl) | H | H |
| 179 | H | H | methyl | methyl | 2-(2-iodo-1-imidazolyl) | H | H |
| 180 | H | H | methyl | methyl | 2-(2-methoxy-1-imidazolyl) | H | H |
| 181 | H | H | methyl | methyl | 2-(2-methylthio-1-imidazolyl) | H | H |
| 182 | H | H | methyl | methyl | 2-(2-cyano-1-imidazolyl) | H | H |
| 183 | H | H | methyl | methyl | 2-(2-chloro-1-imidazolyl) | H | H |
| 184 | H | H | methyl | methyl | 2-(2-methyl-1-imidazolyl) | H | H |
| 185 | H | H | methyl | methyl | 2-(4-methyl-1-imidazolyl) | H | H |
| 186 | H | H | methyl | methyl | 2-(5-methyl-1-imidazolyl) | H | H |
| 187 | H | H | methyl | methyl | 2-(2-fluoromethyl-1-imidazolyl) | H | H |
| 188 | H | H | methyl | methyl | 2-(2-difluoromethyl-1-imidazolyl) | H | H |
| 189 | H | H | methyl | methyl | 2-(2-trifluoromethyl-1-imidazolyl) | H | H |
| 190 | H | H | methyl | methyl | 2-(4,5-dichloro-1-imidazolyl) | H | H |
| 191 | H | H | methyl | methyl | 2-(1-imidazolyl) | 3-fluoro | H |
| 192 | H | H | methyl | methyl | 2-(1-imidazolyl) | 3-chloro | H |
| 193 | H | H | methyl | methyl | 2-(1-imidazolyl) | 3-bromo | H |
| 194 | H | H | methyl | methyl | 2-(1-imidazolyl) | 3-iodo | H |
| 195 | H | H | methyl | methyl | 2-(1-imidazolyl) | 3-cyano | H |
| 196 | H | H | methyl | methyl | 2-(1-imidazolyl) | 3-methyl | H |
| 197 | H | H | methyl | methyl | 2-(1-imidazolyl) | 3-ethyl | H |
| 198 | H | H | methyl | methyl | 2-(1-imidazolyl) | 3-isopropyl | H |
| 199 | H | H | methyl | methyl | 2-(1-imidazolyl) | 3-propyl | H |
| 200 | H | H | methyl | methyl | 2-(1-imidazolyl) | 3-methoxy | H |
| 201 | H | H | methyl | methyl | 2-(1-imidazolyl) | 3-ethoxy | H |
| 202 | H | H | methyl | methyl | 2-(1-imidazolyl) | 3-isopropoxy | H |
| 203 | H | H | methyl | methyl | 2-(1-imidazolyl) | 3-propoxy | H |
| 204 | H | H | methyl | methyl | 2-(1-imidazolyl) | 3-trifluoromethyl | H |
| 205 | H | H | methyl | methyl | 4-cyano | H | H |
| 206 | H | H | methyl | methyl | 4-chloro | H | H |
| 207 | H | methyl | H | H | H | H | H |
| 208 | H | methyl | H | H | 4-fluoro | H | H |
| 209 | H | methyl | H | H | 4-methoxy | H | H |
| 210 | H | methyl | H | H | 2-(1-imidazolyl) | H | H |
| 211 | H | methyl | H | H | 3-(1-imidazolyl) | H | H |
| 212 | H | methyl | H | H | 4-(1-imidazolyl) | H | H |
| 213 | H | methyl | H | H | 4-(1-imidazolyl) | 3-chloro | H |
| 214 | H | methyl | H | ethyl | 4-(1-imidazolyl) | H | H |
| 215 | H | methyl | H | isopropyl | 4-(1-imidazolyl) | H | H |
| 216 | H | methyl | H | propyl | 4-(1-imidazolyl) | H | H |
| 217 | H | methyl | H | hexyl | H | H | H |
| 218 | H | methyl | methyl | methyl | 4-methyl | H | H |
| 219 | H | methyl | methyl | methyl | 4-methoxy | H | H |
| 220 | H | methyl | methyl | methyl | 4-dimethylamino | H | H |
| 221 | H | methyl | methyl | methyl | 4-fluoro | H | H |
| 222 | H | methyl | methyl | methyl | 4-bromo | H | H |
| 223 | H | methyl | methyl | methyl | 4-chloro | H | H |
| 224 | H | methyl | methyl | methyl | 4-cyano | H | H |
| 225 | H | methyl | methyl | methyl | 4-trifluoromethy | H | H |
| 226 | H | methyl | methyl | methyl | 4-(1-imidazolyl) | H | H |
| 227 | H | methyl | methyl | methyl | 4-(2-methyl-1-imidazolyl) | H | H |
| 228 | H | methyl | methyl | methyl | 4-(2-ethyl-1-imidazolyl) | H | H |
| 229 | H | methyl | methyl | methyl | 4-(2-isopropyl-1-imidazolyl) | H | H |
| 230 | H | methyl | methyl | methyl | 4-(2-propyl-1-imidazolyl) | H | H |
| 231 | H | methyl | methyl | methyl | 4-(2-phenyl-1-imidazolyl) | H | H |
| 232 | H | methyl | methyl | methyl | 4-(2-iodo-1-imidazolyl) | H | H |
| 233 | H | methyl | methyl | methyl | 4-(2-methoxyl-1-imidazolyl) | H | H |
| 234 | H | methyl | methyl | methyl | 4-(2-methylthio-1-imidazolyl) | H | H |
| 235 | H | methyl | methyl | methyl | 4-(2-cyano-1-imidazolyl) | H | H |
| 236 | H | methyl | methyl | methyl | 4-(2-chloro-1-imidazolyl) | H | H |
| 237 | H | methyl | methyl | methyl | 4-(2-methyl-1-imidazolyl) | H | H |
| 238 | H | methyl | methyl | methyl | 4-(4-methyl-1-imidazolyl) | H | H |
| 239 | H | methyl | methyl | methyl | 4-(5-methyl-1-imidazolyl) | H | H |
| 240 | H | methyl | methyl | methyl | 4-(2-fluoromethyl-1-imidazolyl) | H | H |
| 241 | H | methyl | methyl | methyl | 4-(2-difluoromethyl-1-imidazolyl) | H | H |
| 242 | H | methyl | methyl | methyl | 4-(2-trimethyl-1-imidazolyl) | H | H |
| 243 | H | methyl | methyl | methyl | 4-(4,5-dichloro-1-imidazolyl) | H | H |
| 244 | H | methyl | methyl | methyl | 4-(1-imidazolyl) | 3-fluoro | H |
| 245 | H | methyl | methyl | methyl | 4-(1-imidazolyl) | 3-chloro | H |
| 246 | H | methyl | methyl | methyl | 4-(1-imidazolyl) | 3-bromo | H |
| 247 | H | methyl | methyl | methyl | 4-(1-imidazolyl) | 3-iodo | H |
| 248 | H | methyl | methyl | methyl | 4-(1-imidazolyl) | 3-cyano | H |
| 249 | H | methyl | methyl | methyl | 4-(1-imidazolyl) | 3-methyl | H |
| 250 | H | methyl | methyl | methyl | 4-(1-imidazolyl) | 3-ethyl | H |
| 251 | H | methyl | methyl | methyl | 4-(1-imidazolyl) | 3-isopropyl | H |
| 252 | H | methyl | methyl | methyl | 4-(1-imidazolyl) | 3-propyl | H |

TABLE 1-continued

| Compound No. | R¹ | R² | R³ | R⁴ | X¹ | X² | X³ |
|---|---|---|---|---|---|---|---|
| 253 | H | methyl | methyl | methyl | 4-(1-imidazolyl) | 3-methoxy | H |
| 254 | H | methyl | methyl | methyl | 4-(1-imidazolyl) | 3-ethoxy | H |
| 255 | H | methyl | methyl | methyl | 4-(1-imidazolyl) | 3-isopropoxy | H |
| 256 | H | methyl | methyl | methyl | 4-(1-imidazolyl) | 3-propoxy | H |
| 257 | H | methyl | methyl | methyl | 4-(1-imidazolyl) | 3-trifluoromethyl | H |
| 258 | H | methyl | methyl | methyl | 4-(2-pyridyl) | H | H |
| 259 | H | methyl | methyl | methyl | 4-(4-pyridyl) | H | H |
| 260 | H | methyl | methyl | methyl | 4-(3-pyridyl) | H | H |
| 261 | H | methyl | methyl | methyl | 3-fluoro | H | H |
| 262 | H | methyl | methyl | methyl | 3-chloro | H | H |
| 263 | H | methyl | methyl | methyl | 3-methyl | H | H |
| 264 | H | methyl | methyl | methyl | 3-methoxy | H | H |
| 265 | H | methyl | methyl | methyl | 3-(1-imidazolyl) | H | H |
| 266 | H | methyl | methyl | methyl | 3-(2-ethyl-1-imidazolyl) | H | H |
| 267 | H | methyl | methyl | methyl | 3-(2-isopropyl-1-imidazolyl) | H | H |
| 268 | H | methyl | methyl | methyl | 3-(2-propyl-1-imidazolyl) | H | H |
| 269 | H | methyl | methyl | methyl | 3-(2-phenyl-1-imidazolyl) | H | H |
| 270 | H | methyl | methyl | methyl | 3-(2-iodo-1-imidazolyl) | H | H |
| 271 | H | methyl | methyl | methyl | 3-(2-methoxyy-1-imidazolyl) | H | H |
| 272 | H | methyl | methyl | methyl | 3-(2-methylthio-1-imidazolyl) | H | H |
| 273 | H | methyl | methyl | methyl | 3-(2-cyano-1-imidazolyl) | H | H |
| 274 | H | methyl | methyl | methyl | 3-(2-chloro-1-imidazolyl) | H | H |
| 275 | H | methyl | methyl | methyl | 3-(2-methyl-1-imidazolyl) | H | H |
| 276 | H | methyl | methyl | methyl | 3-(4-methyl-1-imidazolyl) | H | H |
| 277 | H | methyl | methyl | methyl | 3-(5-methyl-1-imidazolyl) | H | H |
| 278 | H | methyl | methyl | methyl | 3-(2-fluoromethyl-1-imidazolyl) | H | H |
| 279 | H | methyl | methyl | methyl | 3-(2-difluoromethyl-1-imidazolyl) | H | H |
| 280 | H | methyl | methyl | methyl | 3-(2-trifluoromethyl-1-imidazolyl) | H | H |
| 281 | H | methyl | methyl | methyl | 3-(4,5-dichloro-1-imidazolyl) | H | H |
| 282 | H | methyl | methyl | methyl | 3-(1-imidazolyl) | 4-fluoro | H |
| 283 | H | methyl | methyl | methyl | 3-(1-imidazolyl) | 4-chloro | H |
| 284 | H | methyl | methyl | methyl | 3-(1-imidazolyl) | 4-bromo | H |
| 285 | H | methyl | methyl | methyl | 3-(1-imidazolyl) | 4-iodo | H |
| 286 | H | methyl | methyl | methyl | 3-(1-imidazolyl) | 4-cyano | H |
| 287 | H | methyl | methyl | methyl | 3-(1-imidazolyl) | 4-methyl | H |
| 288 | H | methyl | methyl | methyl | 3-(1-imidazolyl) | 4-ethyl | H |
| 289 | H | methyl | methyl | methyl | 3-(1-imidazolyl) | 4-isopropyl | H |
| 290 | H | methyl | methyl | methyl | 3-(1-imidazolyl) | 4-propyl | H |
| 291 | H | methyl | methyl | methyl | 3-(1-imidazolyl) | 4-methoxy | H |
| 292 | H | methyl | methyl | methyl | 3-(1-imidazolyl) | 4-ethoxy | H |
| 293 | H | methyl | methyl | methyl | 3-(1-imidazolyl) | 4-isopropoxy | H |
| 294 | H | methyl | methyl | methyl | 3-(1-imidazolyl) | 4-propoxy | H |
| 295 | H | methyl | methyl | methyl | 3-(1-imidazolyl) | 4-trifluoromethyl | H |
| 296 | H | methyl | methyl | methyl | 3-(1-imidazolyl) | H | H |
| 297 | H | methyl | methyl | methyl | 3-(2-methoxy-1-imidazolyl) | H | H |
| 298 | H | methyl | methyl | methyl | 3-(2-methylthio-1-imidazolyl) | H | H |
| 299 | H | methyl | methyl | methyl | 3-(2-pyridyl) | H | H |
| 300 | H | methyl | methyl | methyl | 3-(3-pyridyl) | H | H |
| 301 | H | methyl | methyl | methyl | 3-(4-pyridyl) | H | H |
| 302 | H | methyl | methyl | methyl | 2-(1-imidazolyl) | H | H |
| 303 | H | methyl | methyl | methyl | 2-(2-methyl-1-imidazolyl) | H | H |
| 304 | H | methyl | methyl | methyl | 2-(2-ethyl-1-imidazolyl) | H | H |
| 305 | H | methyl | methyl | methyl | 2-(2-isopropyl-1-imidazolyl) | H | H |
| 306 | H | methyl | methyl | methyl | 2-(2-propyl-1-imidazolyl) | H | H |
| 307 | H | methyl | methyl | methyl | 2-(2-phenyl-1-imidazolyl) | H | H |
| 308 | H | methyl | methyl | methyl | 2-(2-iodo-1-imidazolyl) | H | H |
| 309 | H | methyl | methyl | methyl | 2-(2-methoxy-1-imidazolyl) | H | H |
| 310 | H | methyl | methyl | methyl | 2-(2-methylthio-1-imidazolyl) | H | H |
| 311 | H | methyl | methyl | methyl | 2-(2-cyano-1-imidazolyl) | H | H |
| 312 | H | methyl | methyl | methyl | 2-(2-chloro-1-imidazolyl) | H | H |
| 313 | H | methyl | methyl | methyl | 2-(2-methyl-1-imidazolyl) | H | H |
| 314 | H | methyl | methyl | methyl | 2-(4-methyl-1-imidazolyl) | H | H |
| 315 | H | methyl | methyl | methyl | 2-(5-methyl-1-imidazolyl) | H | H |
| 316 | H | methyl | methyl | methyl | 2-(2-fluoromethyl-1-imidazolyl) | H | H |
| 317 | H | methyl | methyl | methyl | 2-(2-difluoromethyl-1-imidazolyl) | H | H |
| 318 | H | methyl | methyl | methyl | 2-(2-trifluoromethyl-1-imidazolyl) | H | H |
| 319 | H | methyl | methyl | methyl | 2-(4,5-dichloro-1-imidazolyl) | H | H |
| 320 | H | methyl | methyl | methyl | 2-(1-imidazolyl) | 3-fluoro | H |
| 321 | H | methyl | methyl | methyl | 2-(1-imidazolyl) | 3-chloro | H |
| 322 | H | methyl | methyl | methyl | 2-(1-imidazolyl) | 3-bromo | H |
| 323 | H | methyl | methyl | methyl | 2-(1-imidazolyl) | 3-iodo | H |
| 324 | H | methyl | methyl | methyl | 2-(1-imidazolyl) | 3-cyano | H |
| 325 | H | methyl | methyl | methyl | 2-(1-imidazolyl) | 3-methyl | H |
| 326 | H | methyl | methyl | methyl | 2-(1-imidazolyl) | 3-ethyl | H |
| 327 | H | methyl | methyl | methyl | 2-(1-imidazolyl) | 3-isopropyl | H |
| 328 | H | methyl | methyl | methyl | 2-(1-imidazolyl) | 3-propyl | H |
| 329 | H | methyl | methyl | methyl | 2-(1-imidazolyl) | 3-methoxy | H |
| 330 | H | methyl | methyl | methyl | 2-(1-imidazolyl) | 3-ethoxy | H |
| 331 | H | methyl | methyl | methyl | 2-(1-imidazolyl) | 3-isopropoxy | H |

TABLE 1-continued

| Compound No. | R¹ | R² | R³ | R⁴ | X¹ | X² | X³ |
|---|---|---|---|---|---|---|---|
| 332 | H | methyl | methyl | methyl | 2-(1-imidazolyl) | 3-propoxy | H |
| 333 | H | methyl | methyl | methyl | 2-(1-imidazolyl) | 3-trifluoromethyl | H |
| 334 | H | methyl | methyl | methyl | 3-(2-pyridyl) | H | H |
| 335 | H | methyl | methyl | methyl | 3-(3-pyridyl) | H | H |
| 336 | H | methyl | methyl | methyl | 3-(4-pyridyl) | H | H |
| 337 | H | methyl | methyl | methyl | 3-methoxy | 4-methoxy | 5-methoxy |
| 338 | H | methyl | ethyl | ethyl | 4-(1-imidazolyl) | H | H |
| 339 | H | methyl | ethyl | ethyl | 4-(1-imidazolyl) | 3-fluoro | H |
| 340 | H | methyl | hexyl | hexyl | 4-(1-imidazolyl) | H | H |
| 341 | H | methyl | methyl | hexyl | 4-(1-imidazolyl) | H | H |
| 342 | H | methyl | —CH₂CH₂— | | 4-(1-imidazolyl) | H | H |
| 343 | H | methyl | —CH₂CH₂— | | 3-(1-imidazolyl) | H | H |
| 344 | H | methyl | —CH₂CH₂— | | 2-(1-imidazolyl) | H | H |
| 345 | H | methyl | —CH₂CH₂CH₂— | | H | H | H |
| 346 | H | methyl | —CH₂CH₂CH₂— | | 4-fluoro | H | H |
| 347 | H | methyl | —CH₂CH₂CH₂— | | 4-chloro | H | H |
| 348 | H | methyl | —CH₂CH₂CH₂— | | 4-bromo | H | H |
| 349 | H | methyl | —CH₂CH₂CH₂— | | 4-iodo | H | H |
| 350 | H | methyl | —CH₂CH₂CH₂— | | 4-methyl | H | H |
| 351 | H | methyl | —CH₂CH₂CH₂— | | 4-methoxy | H | H |
| 352 | H | methyl | —CH₂CH₂CH₂— | | 4-trifluoromethyl | H | H |
| 353 | H | methyl | —CH₂CH₂CH₂— | | 4-cyano | H | H |
| 354 | H | methyl | —CH₂CH₂CH₂— | | 4-nitro | H | H |
| 355 | H | methyl | —CH₂CH₂CH₂— | | 4-dimethylamino | H | H |
| 356 | H | methyl | —CH₂CH₂CH₂— | | 4-(1-imidazolyl) | H | H |
| 357 | H | methyl | —CH₂CH₂CH₂— | | 4-(2-methyl-1-imidazolyl) | H | H |
| 358 | H | methyl | —CH₂CH₂CH₂— | | 4-(2-ethyl-1-imidazolyl) | H | H |
| 359 | H | methyl | —CH₂CH₂CH₂— | | 4-(2-isopropyl-1-imidazolyl) | H | H |
| 360 | H | methyl | —CH₂CH₂CH₂— | | 4-(2-propyl-1-imidazolyl) | H | H |
| 361 | H | methyl | —CH₂CH₂CH₂— | | 4-(2-phenyl-1-imidazolyl) | H | H |
| 362 | H | methyl | —CH₂CH₂CH₂— | | 4-(2-iodo-1-imidazolyl) | H | H |
| 363 | H | methyl | —CH₂CH₂CH₂— | | 4-(2-methoxy-1-imidazolyl) | H | H |
| 364 | H | methyl | —CH₂CH₂CH₂— | | 4-(2-methylthio-1-imidazolyl) | H | H |
| 365 | H | methyl | —CH₂CH₂CH₂— | | 4-(2-cyano-1-imidazolyl) | H | H |
| 366 | H | methyl | —CH₂CH₂CH₂— | | 4-(2-chloro-1-imidazolyl) | H | H |
| 367 | H | methyl | —CH₂CH₂CH₂— | | 4-(2-methyl-1-imidazolyl) | H | H |
| 368 | H | methyl | —CH₂CH₂CH₂— | | 4-(4-methyl-1-imidazolyl) | H | H |
| 369 | H | methyl | —CH₂CH₂CH₂— | | 4-(5-methyl-1-imidazolyl) | H | H |
| 370 | H | methyl | —CH₂CH₂CH₂— | | 4-(2-fluoromethyl-1-imidazolyl) | H | H |
| 371 | H | methyl | —CH₂CH₂CH₂— | | 4-(2-difluoromethyl-1-imidazolyl) | H | H |
| 372 | H | methyl | —CH₂CH₂CH₂— | | 4-(2-trifluoro-1-imidazolyl) | H | H |
| 373 | H | methyl | —CH₂CH₂CH₂— | | 4-(4,5-dichloro-1-imidazolyl) | H | H |
| 374 | H | methyl | —CH₂CH₂CH₂— | | 4-(1-imidazolyl) | 3-fluoro | H |
| 375 | H | methyl | —CH₂CH₂CH₂— | | 4-(1-imidazolyl) | 3-chloro | H |
| 376 | H | methyl | —CH₂CH₂CH₂— | | 4-(1-imidazolyl) | 3-bromo | H |
| 377 | H | methyl | —CH₂CH₂CH₂— | | 4-(1-imidazolyl) | 3-iodo | H |
| 378 | H | methyl | —CH₂CH₂CH₂— | | 4-(1-imidazolyl) | 3-cyano | H |
| 379 | H | methyl | —CH₂CH₂CH₂— | | 4-(1-imidazolyl) | 3-methyl | H |
| 380 | H | methyl | —CH₂CH₂CH₂— | | 4-(1-imidazolyl) | 3-ethyl | H |
| 381 | H | methyl | —CH₂CH₂CH₂— | | 4-(1-imidazolyl) | 3-isopropyl | H |
| 382 | H | methyl | —CH₂CH₂CH₂— | | 4-(1-imidazolyl) | 3-propyl | H |
| 383 | H | methyl | —CH₂CH₂CH₂— | | 4-(1-imidazolyl) | 3-methoxy | H |
| 384 | H | methyl | —CH₂CH₂CH₂— | | 4-(1-imidazolyl) | 3-ethoxy | H |
| 385 | H | methyl | —CH₂CH₂CH₂— | | 4-(1-imidazolyl) | 3-isopropoxy | H |
| 386 | H | methyl | —CH₂CH₂CH₂— | | 4-(1-imidazolyl) | 3-propoxy | H |
| 387 | H | methyl | —CH₂CH₂CH₂— | | 4-(1-imidazolyl) | 3-trifluoromethyl | H |
| 388 | H | methyl | —CH₂CH₂CH₂— | | 4-(2-pyridyl) | H | H |
| 389 | H | methyl | —CH₂CH₂CH₂— | | 4-(3-pyridyl) | H | H |
| 390 | H | methyl | —CH₂CH₂CH₂— | | 4-(4-pyridyl) | H | H |
| 391 | H | methyl | —CH₂CH₂CH₂— | | 3-fluoro | H | H |
| 392 | H | methyl | —CH₂CH₂CH₂— | | 3-chloro | H | H |
| 393 | H | methyl | —CH₂CH₂CH₂— | | 3-cyano | H | H |
| 394 | H | methyl | —CH₂CH₂CH₂— | | 3-methyl | H | H |
| 395 | H | methyl | —CH₂CH₂CH₂— | | 3-methoxy | H | H |
| 396 | H | methyl | —CH₂CH₂CH₂— | | 3-(1-imidazolyl) | H | H |
| 397 | H | methyl | —CH₂CH₂CH₂— | | 3-(2-methyl-1-imidazolyl) | H | H |
| 398 | H | methyl | —CH₂CH₂CH₂— | | 3-(2-ethyl-1-imidazolyl) | H | H |
| 399 | H | methyl | —CH₂CH₂CH₂— | | 3-(2-isopropyl-1-imidazolyl) | H | H |
| 400 | H | methyl | —CH₂CH₂CH₂— | | 3-(2-propyl-1-imidazolyl) | H | H |
| 401 | H | methyl | —CH₂CH₂CH₂— | | 3-(2-phenyl-1-imidazolyl) | H | H |
| 402 | H | methyl | —CH₂CH₂CH₂— | | 3-(2-iodo-1-imidazolyl) | H | H |
| 403 | H | methyl | —CH₂CH₂CH₂— | | 3-(2-methoxy-1-imidazolyl) | H | H |
| 404 | H | methyl | —CH₂CH₂CH₂— | | 3-(2-methylthio-1-imidazolyl) | H | H |
| 405 | H | methyl | —CH₂CH₂CH₂— | | 3-(2-cyano-1-imidazolyl) | H | H |
| 406 | H | methyl | —CH₂CH₂CH₂— | | 3-(2-chloro-1-imidazolyl) | H | H |
| 407 | H | methyl | —CH₂CH₂CH₂— | | 3-(2-methyl-1-imidazolyl) | H | H |
| 408 | H | methyl | —CH₂CH₂CH₂— | | 3-(4-methyl-1-imidazolyl) | H | H |
| 409 | H | methyl | —CH₂CH₂CH₂— | | 3-(5-methyl-1-imidazolyl) | H | H |
| 410 | H | methyl | —CH₂CH₂CH₂— | | 3-(2-fluoromethyl-1-imidazolyl) | H | H |

TABLE 1-continued

| Compound No. | R$^1$ | R$^2$ | R$^3$ R$^4$ | X$^1$ | X$^2$ | X$^3$ |
|---|---|---|---|---|---|---|
| 411 | H | methyl | —CH$_2$CH$_2$CH$_2$— | 3-(2-difluoromethyl-1-imidazolyl) | H | H |
| 412 | H | methyl | —CH$_2$CH$_2$CH$_2$— | 3-(2-trifluoromethyl-1-imidazolyl) | H | H |
| 413 | H | methyl | —CH$_2$CH$_2$CH$_2$— | 3-(4,5dichloro-1-imidazolyl) | H | H |
| 414 | H | methyl | —CH$_2$CH$_2$CH$_2$— | 3-(1-imidazolyl) | 4-fluoro | H |
| 415 | H | methyl | —CH$_2$CH$_2$CH$_2$— | 3-(1-imidazolyl) | 4-chloro | H |
| 416 | H | methyl | —CH$_2$CH$_2$CH$_2$— | 3-(1-imidazolyl) | 4-bromo | H |
| 417 | H | methyl | —CH$_2$CH$_2$CH$_2$— | 3-(1-imidazolyl) | 4-iodo | H |
| 418 | H | methyl | —CH$_2$CH$_2$CH$_2$— | 3-(1-imidazolyl) | 4-cyano | H |
| 419 | H | methyl | —CH$_2$CH$_2$CH$_2$— | 3-(1-imidazolyl) | 4-methyl | H |
| 420 | H | methyl | —CH$_2$CH$_2$CH$_2$— | 3-(1-imidazolyl) | 4-ethyl | H |
| 421 | H | methyl | —CH$_2$CH$_2$CH$_2$— | 3-(1-imidazolyl) | 4-isopropyl | H |
| 422 | H | methyl | —CH$_2$CH$_2$CH$_2$— | 3-(1-imidazolyl) | 4-propyl | H |
| 423 | H | methyl | —CH$_2$CH$_2$CH$_2$— | 3-(1-imidazolyl) | 4-methoxy | H |
| 424 | H | methyl | —CH$_2$CH$_2$CH$_2$— | 3-(1-imidazolyl) | 4-ethoxy | H |
| 425 | H | methyl | —CH$_2$CH$_2$CH$_2$— | 3-(1-imidazolyl) | 4-isopropoxy | H |
| 426 | H | methyl | —CH$_2$CH$_2$CH$_2$— | 3-(1-imidazolyl) | 4-propoxy | H |
| 427 | H | methyl | —CH$_2$CH$_2$CH$_2$— | 3-(1-imidazolyl) | 4-trifluoromethyl | H |
| 428 | H | methyl | —CH$_2$CH$_2$CH$_2$— | 3-(1-imidazolyl) | H | H |
| 429 | H | methyl | —CH$_2$CH$_2$CH$_2$— | 3-(2-methoxy-1-imidazolyl) | H | H |
| 430 | H | methyl | —CH$_2$CH$_2$CH$_2$— | 3-(2-methylthio-1-imidazolyl) | H | H |
| 431 | H | methyl | —CH$_2$CH$_2$CH$_2$— | 3-(2-pyridyl) | H | H |
| 432 | H | methyl | —CH$_2$CH$_2$CH$_2$— | 3-(3-pyridyl) | H | H |
| 433 | H | methyl | —CH$_2$CH$_2$CH$_2$— | 3-(4-pyridyl) | H | H |
| 434 | H | methyl | —CH$_2$CH$_2$CH$_2$— | 3-trifluoromethyl | 4-chloro | H |
| 435 | H | methyl | —CH$_2$CH$_2$CH$_2$— | 3-methoxy | 4-methoxy | H |
| 436 | H | methyl | —CH$_2$CH$_2$CH$_2$— | 3-(1-pyrrolyl) | H | H |
| 437 | H | methyl | —CH$_2$CH$_2$CH$_2$— | 4-(1-pyrazolyl) | H | H |
| 438 | H | methyl | —CH$_2$CH$_2$CH$_2$— | 4-(1-(1,2,4-triazolyl)) | H | H |
| 439 | H | methyl | —CH$_2$CH$_2$CH$_2$— | 4-(1-(2-pyridonyl)) | H | H |
| 440 | H | methyl | —CH$_2$CH$_2$CH$_2$— | 4-(2-imidazolyl) | H | H |
| 441 | H | methyl | —CH$_2$CH$_2$CH$_2$— | 4-(2-pyridyl) | H | H |
| 442 | H | methyl | —CH$_2$CH$_2$CH$_2$— | 4-(3-pyridyl) | H | H |
| 443 | H | methyl | —CH$_2$CH$_2$CH$_2$— | 4-(4-pyridyl) | H | H |
| 444 | H | methyl | —CH$_2$CH$_2$CH$_2$— | 4-(1-thiazolyl) | H | H |
| 445 | H | methyl | —CH$_2$CH$_2$CH$_2$— | 4-(2-thiazolyl) | H | H |
| 446 | H | methyl | —CH$_2$CH$_2$CH$_2$— | 4-(1-oxazolyl) | H | H |
| 447 | H | methyl | —CH$_2$CH$_2$CH$_2$— | 4-(2-oxazolyl) | H | H |
| 448 | H | methyl | —CH$_2$CH$_2$CH$_2$— | 4-(1-pyrrolyl) | H | H |
| 449 | H | methyl | —CH$_2$CH$_2$CH$_2$— | 4-(1-pyridazinyl) | H | H |
| 450 | H | methyl | —CH$_2$CH$_2$CH$_2$— | 4-(1-pyrimidinyl) | H | H |
| 451 | H | methyl | —CH$_2$CH$_2$CH$_2$— | 2-(1-imidazolyl) | H | H |
| 452 | H | methyl | —CH$_2$CH$_2$CH$_2$— | 2-(2-methyl-1-imidazolyl) | H | H |
| 453 | H | methyl | —CH$_2$CH$_2$CH$_2$— | 2-(2-ethyl-1-imidazolyl) | H | H |
| 454 | H | methyl | —CH$_2$CH$_2$CH$_2$— | 2-(2-isopropyl-1-imidazolyl) | H | H |
| 455 | H | methyl | —CH$_2$CH$_2$CH$_2$— | 2-(2-propyl-1-imidazolyl) | H | H |
| 456 | H | methyl | —CH$_2$CH$_2$CH$_2$— | 2-(2-phenyl-1-imidazolyl) | H | H |
| 457 | H | methyl | —CH$_2$CH$_2$CH$_2$— | 2-(2-iodo-1-imidazolyl) | H | H |
| 458 | H | methyl | —CH$_2$CH$_2$CH$_2$— | 2-(2-methoxy-1-imidazolyl) | H | H |
| 459 | H | methyl | —CH$_2$CH$_2$CH$_2$— | 2-(2-methylthio-1-imidazolyl) | H | H |
| 460 | H | methyl | —CH$_2$CH$_2$CH$_2$— | 2-2-cyano-1-imidazolyl) | H | H |
| 461 | H | methyl | —CH$_2$CH$_2$CH$_2$— | 2-(2-chloro-1-imidazolyl) | H | H |
| 462 | H | methyl | —CH$_2$CH$_2$CH$_2$— | 2-(2-methyl-1-imidazolyl) | H | H |
| 463 | H | methyl | —CH$_2$CH$_2$CH$_2$— | 2-(4-methyl-1-imidazolyl) | H | H |
| 464 | H | methyl | —CH$_2$CH$_2$CH$_2$— | 2-(5-methyl-1-imidazolyl) | H | H |
| 465 | H | methyl | —CH$_2$CH$_2$CH$_2$— | 2-(2-fluoromethyl-1-imidazolyl) | H | H |
| 466 | H | methyl | —CH$_2$CH$_2$CH$_2$— | 2-(2-difluoromethyl-1-imidazolyl) | H | H |
| 467 | H | methyl | —CH$_2$CH$_2$CH$_2$— | 2-(2-trifluoromethyl-1-imidazolyl) | H | H |
| 469 | H | methyl | —CH$_2$CH$_2$CH$_2$— | 2-(1-imidazolyl) | 3-fluoro | H |
| 470 | H | methyl | —CH$_2$CH$_2$CH$_2$— | 2-(1-imidazolyl) | 3-chloro | H |
| 471 | H | methyl | —CH$_2$CH$_2$CH$_2$— | 2-(1-imidazolyl) | 3-bromo | H |
| 472 | H | methyl | —CH$_2$CH$_2$CH$_2$— | 2-(1-imidazolyl) | 3-iodo | H |
| 473 | H | methyl | —CH$_2$CH$_2$CH$_2$— | 2-(1-imidazolyl) | 3-cyano | H |
| 474 | H | methyl | —CH$_2$CH$_2$CH$_2$— | 2-(1-imidazolyl) | 3-methyl | H |
| 475 | H | methyl | —CH$_2$CH$_2$CH$_2$— | 2-(1-imidazolyl) | 3-ethyl | H |
| 476 | H | methyl | —CH$_2$CH$_2$CH$_2$— | 2-(1-imidazolyl) | 3-isopropyl | H |
| 477 | H | methyl | —CH$_2$CH$_2$CH$_2$— | 2-(1-imidazolyl) | 3-propyl | H |
| 478 | H | methyl | —CH$_2$CH$_2$CH$_2$— | 2-(1-imidazolyl) | 3-methoxy | H |
| 479 | H | methyl | —CH$_2$CH$_2$CH$_2$— | 2-(1-imidazolyl) | 3-ethoxy | H |
| 480 | H | methyl | —CH$_2$CH$_2$CH$_2$— | 2-(1-imidazolyl) | 3-isopropoxy | H |
| 481 | H | methyl | —CH$_2$CH$_2$CH$_2$— | 2-(1-imidazolyl) | 3-propoxy | H |
| 482 | H | methyl | —CH$_2$CH$_2$CH$_2$— | 2-(1-imidazolyl) | 3-trifluoromethyl | H |
| 483 | H | methyl | —CH$_2$CH$_2$CH$_2$— | 2-(2-pyridyl) | H | H |
| 484 | H | methyl | —CH$_2$CH$_2$CH$_2$— | 2-(3-pyridyl) | H | H |
| 485 | H | methyl | —CH$_2$CH$_2$CH$_2$— | 2-(4-pyridyl) | H | H |
| 486 | H | methyl | —CH$_2$CH$_2$CH$_2$— | 2-cyano | H | H |
| 487 | H | methyl | —CH$_2$CH$_2$CH$_2$— | 3-nitro | 4-methoxy | H |
| 488 | H | methyl | —CH$_2$CH$_2$CH$_2$— | 3-chloro | 4-chloro | H |
| 489 | H | methyl | —CH$_2$CH$_2$CH$_2$— | 4-sulfamoyl | H | H |
| 490 | H | methyl | —CH$_2$CH$_2$CH$_2$— | 3-propoxy | H | H |

TABLE 1-continued

| Compound No. | R¹ | R² | R³ | R⁴ | X¹ | X² | X³ |
|---|---|---|---|---|---|---|---|
| 491 | H | methyl | —CH₂CH₂CH₂— | | 3-chloro | 4-chloro | H |
| 492 | H | methyl | —CH₂CH₂CH₂— | | 3-cyano | 4-cyano | H |
| 493 | H | methyl | —CH₂CH₂CH₂— | | 2-methoxy | 4-methoxy | 5-methoxy |
| 494 | H | methyl | —CH₂CH₂CH₂CH₂— | | H | H | H |
| 495 | H | methyl | —CH₂CH₂CH₂CH₂— | | 4-fluoro | H | H |
| 496 | H | methyl | —CH₂CH₂CH₂CH₂— | | 4-(1-imidazolyl) | H | H |
| 497 | H | methyl | —(CH₂)₅— | | H | H | H |
| 498 | H | ethyl | —(CH₂)₅— | | 4-(1-imidazolyl) | H | H |
| 499 | H | ethyl | —CH₂CH₂CH₂— | | 4-(1-imidazolyl) | H | H |
| 500 | H | ethyl | H | methyl | 4-(1-imidazolyl) | H | H |
| 501 | H | ethyl | methyl | methyl | 4-(1-imidazolyl) | H | H |
| 502 | H | isopropyl | —CH₂CH₂CH₂— | | 4-(1-imidazolyl) | H | H |
| 503 | H | isoamyl | —CH₂CH₂CH₂— | | 4-(1-imidazolyl) | H | H |
| 504 | H | cyclopropyl | —CH₂CH₂CH₂— | | 4-(1-imidazolyl) | H | H |
| 505 | methyl | methyl | —CH₂CH₂CH₂— | | 4-(1-imidazolyl) | H | H |
| 506 | methyl | ethyl | —CH₂CH₂CH₂— | | 4-(1-imidazolyl) | H | H |
| 507 | —CH₂CH₂— | | —CH₂CH₂CH₂— | | 4-(1-imidazolyl) | H | H |
| 508 | —CH₂CH₂CH₂— | | —CH₂CH₂CH₂— | | 4-(1-imidazolyl) | H | H |
| 509 | —(CH₂)₄— | | —CH₂CH₂CH₂— | | 3-(1-imidazolyl) | 4-methoxy | H |
| 510 | —(CH₂)₄— | | —CH₂CH₂CH₂— | | 4-(1-imidazolyl) | H | H |
| 511 | —(CH₂)₅— | | —CH₂CH₂CH₂— | | 4-(1-imidazolyl) | H | H |
| 512 | H | methyl | methyl | methyl | 3-(2-iodo-1-imidazolyl) | 4-methoxy | H |
| 513 | H | methyl | methyl | methyl | 3-(2-methyl-1-imidazolyl) | 4-methoxy | H |
| 514 | H | methyl | —CH₂CH₂CH₂— | | 4-(2-bromo-1-imidazolyl) | H | H |
| 515 | H | methyl | methyl | methyl | 3-(2-methoxy-1-imidazolyl) | 4-methoxy | H |
| 516 | H | methyl | methyl | methyl | 3-(2-iodo-1-imidazolyl) | 4-ethoxy | H |
| 517 | H | methyl | methyl | methyl | 3-(2-methyl-1-imidazolyl) | 4-ethoxy | H |
| 518 | H | methyl | —CH₂CH₂CH₂— | | 4-(1-imidazolyl) | 2-methoxy | H |

The process for producing the compounds of the present invention will now be explained. The compounds of the present invention can be produced, for example, by the following route.

Route A

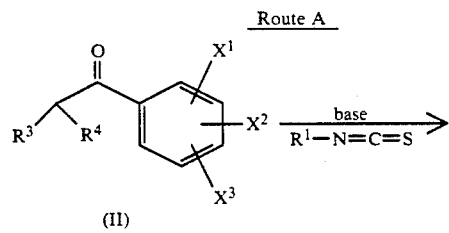

(II)

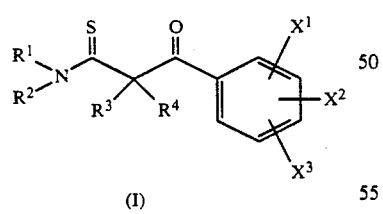

(I)

(wherein R² represents hydrogen atom.)

Route B

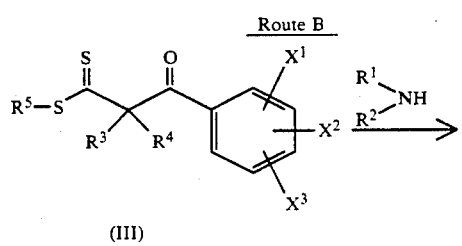

(III)

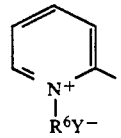

-continued
Route B

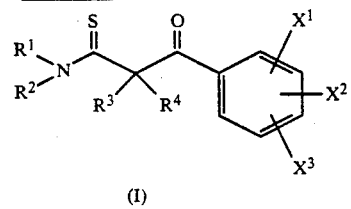

(I)

[In the above formula, R¹, R², R³, R⁴, X¹, X² and X³ are the same as defined above; and R⁵ represents an alkyl group of C₁ to C₅ or (wherein R⁶ represents an alkyl group of C₁ to C₅, and Y represents a halogen atom.)]

Synthesis Route A

Synthesis Route A is a process for producing the compound (I) of the present invention, by reacting the acetophenone derivative (II) with an isothiocyanate compound. That is, the compounds (I) of the present invention can be produced by reacting the acetophenone derivative (II) with an isothiocyanate compounds in the presence of a base, for example, sodium hydride, butyl lithium, lithium diisopropylamide or potassium t-butoxide, in a solvent at −100° to 100° C. for several minutes to several tens hours. Examples of such solvent includes tetrahydrofuran, diethyl ether, N,N-dimethylformamide, and the like, without specific limitation, if not involved in the reaction.

Synthetic Route B

Synthetic Route B is a process for producing the compounds (I) of the present invention, by reacting the dithioester derivative (III) with a corresponding amine compound. That is, the dithioester derivative (III) and the amine compound are reacted together in the presence of a solvent not involved in the reaction, for example, polar solvents such as water, methanol, ethanol, isopropanol, N,N-dimethylformamide, tetrahydrofuran, diethyl ether, etc. or a mixed solvent thereof, or an aromatic hydrocarbon such as benzene, toluene, xylene, etc., or in the absence of a solvent, at −20° to 140° C. for several minutes to 48 hours.

Dithioester derivatives (III) can be synthesized, for example, according to the method described hereinbelow. That is, the acetophenone derivative (II) reacts with carbon disulfide in a solvent not involved in the reaction such as tetrahydrofuran, diethyl ether, N,N-dimethylformamide, etc., in the presence of a base (including, for example, butyl lithium, lithium diisopropylamide or potassium t-butoxide or the like) at −100° to 50° C. for several minutes to several tens hours, and to the resulting solution is then added a halogenated alkyl for reaction at −50° to 50° C. for several minutes to several tens hours. Otherwise, a 2-halo-1-alkylpyridinium salt is added to the resulting solution along with a base, for example, triethylamine, pyridine, etc., for reaction at −20° to 100° C. for several minutes to several tens hours to produce the compound (III).

Other than the routes described above, the compounds of the present invention can be produced through a reaction comprising introducing a substituent (including, for example, nitration reaction) into the benzene ring of the β-oxo-β-benzenepropanethioamide derivatives.

The compounds of the present invention can be prepared into a variety of acid addition salts, if the compound has a basic substituent such as nitrogen-containing aromatic heterocyclic group or dialkylamino group, and such salts can be produced by dissolving the compound of the present invention in an appropriate solvent such as ethanol, ether, etc., thereafter adding an acid as it is or after dissolved in a solvent.

The compounds of the present invention have potassium channel opening action and are useful for treatment of hypertension, asthma, hypersensitive colon syndrome, and enteriris through pharmacological actions including blood vessel dilation, bronchial tract dilation, relaxation of gastrointestinal tract smooth muscle, and the like. The present compounds are administered to humans through oral administration or parenteral administration according to routine methods. The formulation for oral dose includes granules, microfine granules, powders, tablets, hard capsules, soft capsules, syrups, emulsions, suspensions, or liquid preparations or the like. The formulation for parenteral dose includes injections, suppositories, transcutaneous agents and the like.

The compound represented by the above general formula (I) or pharmaceutically acceptable salts thereof are contained in the above formulations, together with routine pharmaceutical additives such as solid or liquid pharmaceutical carriers or excipients, stabilizers, lubricants, sweet flavors, preservatives, suspending agents or the like.

Examples of the solid carriers to be used include galactose, kaolin, sucrose, crystal cellulose, corn starch, talc, agar, pectin, acasia, magnesium stearate, lecithin, sodium chloride, and the like. Examples of the liquid carriers include syrup, glycerine, peanut oil, polyvinylpyrrolidone, olive oil, ethanol, benzyl alcohol, propylene glycol, water and the like.

The dose of the compound of the present invention is 0.01 mg to 1000 mg/day, preferably 0.1 mg to 100 mg/day for oral administration, but preferably, the dose is appropriately modified, depending on the age, sex, pathology, symptom, the presence or absence of concurrent therapy, and the like. The dosage may be administered once/day, or may be divided into several times/day with an appropriate interval.

In producing solid formulations, excipients such as lactose, sucrose, carbohydrate, talc, cellulose, dextrin, kaolin, calcium carbonate and the like are employed. In case of liquid formulations for oral administration, such as syrups, emulsions, suspensions or liquid preparations, the above liquid carriers generally employed are used along with an appropriate auxiliary such as a lubricant, a suspension auxiliary, a sweet flavor, a flavor, a coloring agent or a preservative.

EXAMPLES

The present invention will now be explained in details with reference to examples, but the invention is not limited to the following examples without departing from the gist thereof.

EXAMPLE 1

Synthesis of 4-( 1-imidazolyl)-N-methyl-β-oxo-α, α-trimethylenebenzenepropanethioamide (Compound No. 36 of Table 1)

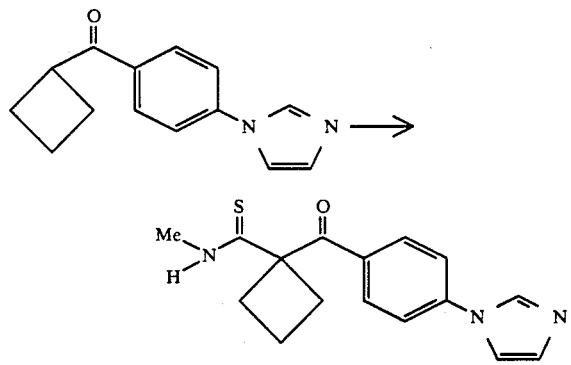

(In the above formula, Me represents methylene group.)

4-( 1-Cyclobutylcarbonylphenyl)-1-imidazole (2.65 g (11.7 mmol)) was dissolved in 20 ml of tetrahydrofuran, followed by dropwise addition of a solution of 1.88 g (16.8 mmol) of potassium t-butoxide in 10 ml of tetrahydrofuran at −20° C. and subsequent agitation at the same temperature for 30 minutes. To the reaction solution was added dropwise a solution of 1.73 g (234 mmol) of methyl isothiocyanate in 5 me of tetrahydrofuran while keeping the temperature at −20° C. or less. After the completion of the dropwise addition, the reaction temperature was gradually raised for effecting agitation at 0° C. for 2 hours.

To the reaction solution was added water for extraction into chloroform. The organic phase was washed in water and aqueous saturated sodium chloride solution, dried over sodium sulfate for distilling off the solvent, and the resulting residue was purified by silica gel column chromatography (elution solvent; chloroform/methanol=50/1), to yield a crude crystal product. The product was recrystallized in toluene, to produce 1.45 g of 4-(1-imidazolyl)-N-methyl-β-oxo-α,α-trimethylenebenzenepropanethioamide. (Yield: 41.4%)

Melting point: 185°–187° C.

IR absorption spectrum (KBr tablet): 1670 cm$^{-1}$ (C=O).

NMR (solvent; CDCl$_3$, δ value (ppm)): 1.83 (m, 1H), 2.07 (m, 1H), 2.82 (m, 2H), 2.98 (m, 2H), 3.12 (d, 3H), 7.23 (s, 1H), 7.25–7.3 (brd, 1H), 7.33 (s, 1H), 7.46 (d, 2H), 7.93 (s, 1H), 8.14 (d, 2H).

EXAMPLES 2 to 37

Following the same method as in Example 1, the compounds shown in Table 2 were produced.

TABLE 2

| Example No. | Compound No. | Melting point (°C.) | IR (cm$^{-1}$) | NMR Solvent; CDCl$_3$ [(CD$_3$)$_2$SO in Example 3], δ value (ppm) |
|---|---|---|---|---|
| 2 | 208 | 106–108 | 1680 | 1.60(d, 3H), 3.17(3H, d), 5.11(q, 1H), 7.14–7.21(m, 2H), 8.10–8.16(m, 2H), 8.60(broad, 1H) |
| 3 | 212 | 217–219 | 1685 | 1.37(d, 3H), 2.94(d, 3H), 4.83(q, 1H), 7.13(s, 1H), 7.78(d, 2H), 7.85(s, 1H), 7.98(d, 2H), 8.39(s, 1H), 10.51(1H, broad)DMSO-d6 |
| 4 | 220 | 189–190 | 1643 | 1.61(s, 6H), 3.04(s, 6H), 3.12(d, 3H), 6.61(d, 2H), 7.87(d, 2H) |
| 5 | 221 | 120–122 | 1660 | 1.62(s, 6H), 3.18(d, 3H), 7.02–7.10(m, 2H), 7.30(broad, 1H), 7.89–7.96(m, 2H) |
| 6 | 222 | 145 | 1664 | 1.61(s, 6H), 3.17(d, 3H), 7.2–7.3(broad, 1H), 7.54(m, 2H), 7.74(m, 2H) |
| 7 | 226 | 179 | 1670 | 1.65(s, 6H), 3.20(d, 3H), 7.25(s, 1H), 7.3–7.4(broad, 1H), 7.44(d, 2H), 7.96(1s, 1H), 8.06(d, 2H) |
| 8 | 261 | 108.5–110 | 1665 | 1.62(s, 6H), 3.19(d, 3H), 7.21(m, 1H), 7.2–7.3(broad, 1H), 7.37(m, 1H), 7.56(m, 1H), 7.66(m, 1H) |
| 9 | 262 | 101–101.5 | 1670 | 1.62(s, 6H), 3.19(d, 3H), 7.2–7.4(broad, 1H), 7.32(m, 1H), 7.48(m, 1H), 7.75(m, 1H), 7.85(m, 1H) |
| 10 | 342 | 154.5–155.5 | 1670 | 1.50(m, 2H), 1.86(m, 2H), 3.11(d, 3H), 7.26(s, 1H), 7.35(s, 1H), 7.49(d, 2H), 7.98(s, 1H), 8.19(d, 2H) |
| 11 | 345 | 113–114 | 1647 | 1.78(m, 1H), 2.05(m, 1H), 2.83(m, 2H), 2.96(m, 2H), 3.11(d, 3H), 7.41(m, 3H), 7.53(t, 2H), 7.96(d, 2H) |
| 12 | 346 | 115–116 | 1660 | 1.80(m, 1H), 2.02(m, 1H), 2.83(m, 2H), 2.98(m, 2H), 3.11(d, 3H), 7.09(t, 2H), 7.2–7.4(broad, 1H), 8.02(m, 2H) |
| 13 | 347 | 151.5 | 1648 | 1.81(m, 1H), 2.202(m, 1H), 2.75–2.85(m, 2H), 2.90–3.00(m, 2H), 3.11(d, 3H), 7.2–7.3(drs, 1H), 7.40(m, 2H), 7.93(m, 2H) |
| 14 | 348 | 162–163 | 1648 | 1.81(m, 1H), 2.02(m, 1H), 2.75–2.85(m, 2H), 2.90–3.00(m, 2H), 3.11(d, 3H), 7.2–7.3(broad, 1H), 7.55(m, 2H), 7.85(m, 2H) |
| 15 | 352 | 11.8.5–119 | 1672 | 1.82(m, 1H), 2.06(m, 1H), 2.75–2.85(m, 2H), 2.93–3.05(m, 2H), 3.12(d, 3H), 7.2–7.3(broad, 1H), 7.68(m, 2H), 8.10(m, 2H) |
| 16 | 357 | 230 | 1670 | 1.80(m, 1H), 2.05(m, 1H), 2.41(s, 3H), 2.88(m, 2H), 3.00(m, 2H), 3.14(d, 3H), 7.02(s, 1H), 7.05(s, 1H), 7.3–7.4(broad, 1H), 7.37(d, 2H), 8.14(d, 2H) |
| 17 | 358 | 135–135.5 | 1685 | 1.28(t, 3H), 1.80(m, 1H), 2.17(m, 1H), 2.70(q, 2H), 2.87(m, 2H), 3.00(m, 2H), 3.14(d, 3H), 6.99(s, 1H), 7.07(s, 1H), 7.35(d, 2H), 7.3–7.4(broad, 1H), 8.13(d, 2H) |
| 18 | 359 | 193–195 | 1675 | 1.26(d, 6H), 1.76–1.91(m, 1H), 2.01–2.18(m, 1H), 2.80–3.08(m, 5H), 3.15(d, 3H), 6.94(d, 1H), 7.08(d, 1H), 7.34(broad, 1H), 7.35(d, 2H), 8.13(d, 2H) |
| 19 | 360 | 162–164 | 1675 | 0.90(t, 3H), 1.65–1.90(m, 4H), 2.00–2.15(m, 1H) 2.64(t, 2H), 2.80–2.92(m, 2H), 2.97–3.08(m, 2H), 3.15(d, 3H), 6.98(d, 1H), 7.08(d, 1H), 7.35(d, 2H), 7.42(broad, 1H), 8.12(d, 2H) |
| 20 | 361 | amorphous | 1670 | 1.76–1.90(m, 1H), 2.00–2.16(m, 1H), 2.80–2.89(m, 2H), 2.93–3.08(m, 2H), 3.13(d, 3H), 7.17(d, 1H), 7.24–7.39(m, 9H), 8.01(d, 2H) |
| 21 | 362 | 163–165 (decomposition) | 1670 | 1.76–1.88(m, 1H), 2.01–2.14(m, 1H), 2.80–2.92(m, 2H), 2.97–3.08(m, 2H), 3.15(d, 3H), 7.20(d, 1H), 7.23(d, 1H), 7.34(broad, 1H), 7.44(d, 2H), 8.14(d, 2H) |
| 22 | 368 | 180 | 1660 | 1.80(m, 1H), 2.05(m, 1H), 2.29(s, 3H), 2.80(m, 2H), 2.98(m, 2H), 3.12(d, 3H), 7.06(s, 1H), 7.2–7.4(broad, 1H), 7.40(d, 2H), 7.65(s, 1H), 8.12(d, 2H) |
| 23 | 369 | 220–220.5 | 1685 | 1.80(m, 1H), 2.00(m, 1H), 2.22(s, 3H), 2.86(m, 2H), 3.00(m, 2H), 3.14(d, 3H), 6.93(s, 1H), 7.36(d, 2H), 7.4–7.5(broad, 1H), 7.58(s, 1H), 8.16(d, 2H) |
| 24 | 373 | 184–186 | 1665 | 1.76–1.92(m, 1H), 2.00–2.18(m, 1H), 2.79–2.91(m, 2H), 2.96–3.08(m, 2H), 3.14(d, 3H), 7.33(broad, 1H), 7.45(d, 2H), 7.57(s, 1H), 8.18(d, 2H) |
| 25 | 374 | 162–164 | 1670 | 1.83(m, 1H), 2.07(m, 1H), 2.87(m, 2H), 2.99(m, 2H), 3.13(d, 3H), 7.25(s, 1H), 7.32(s, 1H), 7.7–7.9(broad, 1H), 7.47(t, 1H), 7.92(s, 1H), 7.95(m, 2H) |
| 26 | 375 | 173 | 1670 | 1.83(m, 1H), 2.05(m, 1H), 2.80–2.90(m, 2H), 2.95–3.02(m, 2H), 3.12(d, 3H), 7.19(m, 1H), 7.22(m, 1H), 7.2–7.3(broad, 1H), 7.38(d, 1H), 7.75(s, 1H), 8.02(m, 1H), |

TABLE 2-continued

| Example No. | Compound No. | Melting point (°C.) | IR (cm⁻¹) | NMR Solvent; CDCl₃ [(CD₃)₂SO in Example 3], δ value (ppm) |
|---|---|---|---|---|
| 27 | 378 | 156 | 2250, 1680 | 8.23(d, 1H) 1.85(m, 1H), 2.05(m, 1H), 2.80–2.90(m, 2H), 2.95–3.03(m, 2H), 3.12(d, 3H), 7.29(s, 1H), 7.41(m, 1H), 7.5–7.6(broad, 1H), 7.50–7.54(d, 1H), 7.94(s, 1H), 8.38–8.42(m, 1H), 8.50(m, 1H) |
| 28 | 392 | 119.5–120 | 1663 | 1.81(m, 1H), 2.02(m, 1H), 2.75–2.85(m, 2H), 2.92–3.05(m, 2H), 3.11(d, 3H), 7.2–7.3(broad, 1H), 7.35(t, 1H), 7.50(m, 1H), 7.85(d, 1H), 7.97(d, 1H) |
| 29 | 396 | 198 | 1671 | 1.83(m, 1H), 2.05(m, 1H), 2.80–2.90(m, 2H), 2.95(m, 2H), 3.13(d, 3H), 7.24(s, 1H), 7.2–7.3(broad, 1H), 7.34(s, 1H), 7.50–7.57(m, 2H), 7.80–7.93(m, 2H), 8.14(s, 1H) |
| 30 | 404 | 147.5–149.5 | 1670 | 1.83(m, 1H), 2.07(m, 1H), 2.62(s, 3H), 2.90(m, 2H), 2.99(m, 2H), 3.13(d, 3H), 7.13(s, 1H), 7.18(s, 1H), 7.25–7.4(broad, 1H), 7.5–7.6(m, 2H), 8.02–8.06(m, 2H) |
| 31 | 434 | 137 | 1666 | 1.82(m, 1H), 2.04(m, 1H), 2.75–2.85(m, 2H), 2.93–3.03(m, 2H), 3.11(d, 3H), 7.2–7.3(broad, 1H), 7.55(m, 1H), 8.12(m, 1H), 8.38(m, 1H) |
| 32 | 437 | 177–179 | 1655 | 1.80(m, 1H), 2.06(m, 1H). 2.85(m, 2H), 3.01(m, 2H), 3.12(d, 3H), 6.51(dd, 1H), 7.2–7.4(broad, 1H), 7.75(d, 1H), 7.77(d, 2H), 7.98(d, 1H), 8.09(d, 2H) |
| 33 | 438 | 200–200.5 | 1665 | 1.80(m, 1H), 2.06(m, 1H), 2.87(m, 2H), 3.00(m, 2H), 3.12(d, 3H), 7.2–7.3(broad, 1H), 7.79(d, 2H), 8.13(s, 1H), 8.16(d, 2H), 8.63(s, 1H) |
| 34 | 439 | 209–209.5 | 1670 | 1.80(m, 1H), 2.05(m, 1H), 2.83(m, 1H). 2.98(m, 1H), 3.12(d, 3H), 6.27(t, 1H), 6.67(d, 1H), 7.29(m, 1H), 7.2–7.3(broad, 1H), 7.40(m, 1H), 7.46(d, 2H), 8.13(d, 2H) |
| 35 | 495 | 110–111 | 1662 | 1.58(m, 2H), 1.77(m, 2H), 3.11(d, 3H), 7.05(m, 2H), 7.1–7.2(broad, 1H), 8.04(m, 2H) |
| 36 | 496 | 175–176 | 1673 | 1.59(m, 2H), 1.79(m, 2H), 2.4–2.6(m, 4H), 3.13(d, 3H), 7.23(s, 1H), 7.33(s, 1H), 7.44(d, 2H), 7.93(s, 1H), 8.15(d, 2H) |
| 37 | 500 | 206.5–207.5 | 1680 | 1.27(t, 3H), 1.61(d, 3H), 3.68(m, 2H), 5.15(q, 1H), 7.2–7.3(broad, 1H), 7.26(s, 1H), 7.53(d, 2H), 7.99(s, 1H), 8.24(d, 2H) |
| 38 | 514 | 205–207 | 1678 | 1.76–1.90(m, 1H), 2.01–2.15(m, 1H), 2.80–2.91(m, 2H), 2.96–3.08(m, 2H), 3.14(d, 3H), 7.16(s, 2H), 7.34(d, 1H), 7.46(dd, 2H), 8.14(dd, 2H) |
| 39 | 518 | 168 | 1658 | 1.75(m, 1H), 2.04(m, 1H), 2.63(m, 2H), 2.90(m, 2H), 3.17(d, 3H), 3.88(s, 3H), 6.89(d, 1H), 7.04(dd, 1H), 7.23(d, 1H), 7.31(d, 1H), 7.60(broad, 1H), 7.78(d, 1H) |

REFERENCE EXAMPLE 1

Synthesis of 4-(1-imidazolyl)-S-methyl-β-oxo-α,α-trimethylenebenzenepropane dithioester

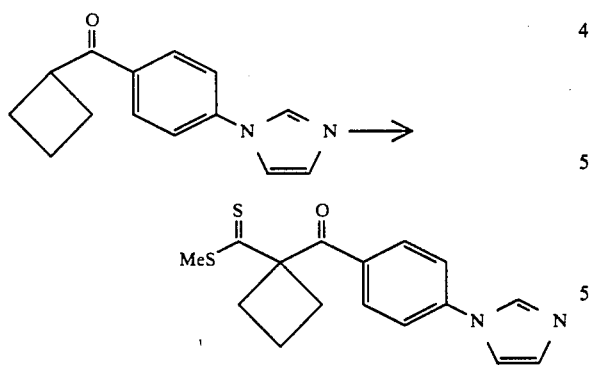

4-(1-Cyclobutylcarbonylphenyl)-1-imidazole (1.00 g (4.42 mmol)) was dissolved in 15 ml of tetrahydrofuran, followed by dropwise addition of a solution of 0.64 g (5.7 mmol) of potassium t-butoxide in 7 ml of tetrahydrofuran at −30° C. and subsequent agitation at the same temperature for 20 minutes. To the reaction solution was then added dropwise a solution of 0.50 g (6.6 mmol) of carbon disulfide in 4 ml of tetrahydrofuran at −20° C. for agitation for 20 minutes, followed by dropwise addition of 0.83 g (5.9 mmol) of methyl iodide in 4 ml of tetrahydrofuran at the same temperature. The reaction temperature was gradually raised to room temperature for effecting agitation for 30 minutes, followed by addition of water for extraction into chloroform. After washing in water and aqueous saturated sodium chloride solution and drying over sodium sulfate for distilling off the solvent, the resulting crude crystal product was recrystallized in a mixed solvent of toluene and hexane, to yield 1.06 g of 4-(1-imidazolyl)-S-methyl-β-oxo-α,α-trimethylene benzenepropane dithioester. (Yield: 75.4%)

EXAMPLE 40

Synthesis of N-ethyl-4-(1-imidazolyl)-β-oxo-α,α-trimethylenebenzenepropane thioamide (Compound No. 499 of Table 1)

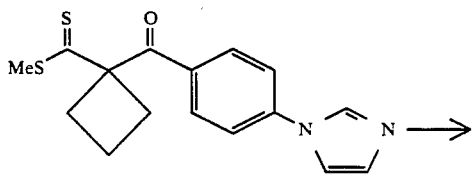

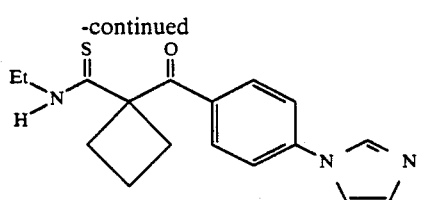

(In the above formula, Me represents methylene group; and Et represents ethyl group.)

4-(1-Imidazolyl) -S-methyloxo-α, α-trimethylene-β-benzenepropane dithioester (315 mg (1.00 mmol)) was dissolved in 10 ml of isopropanol, followed by addition of a solution of 0.18 g (3.9 mmol) of ethylamine in 0.8 ml of isopropanol for agitation at room temperature for 2 days. Adding water for extraction into chloroform, the chloroform phase was washed in water and aqueous saturated sodium chloride solution, dried over sodium sulfate for distilling off the solvent, and the resulting residue was purified by silica gel column chromatography (elution solvent; chloroform), to yield 245 mg of N-ethyl-4-(1-imidazolyl)-β-oxo-α, α-trimethylenebenzenepropanethioamide. (Yield: 78.6%)

Melting point: 157°–157° C.

IR absorption spectrum (KBr tablet) 167 cm$^{-1}$ (C=O).

NMR (solvent; CDCl$_3$, δ value (ppm)): 1.16 (s, 3H), 1.81 (m, 1H), 2.07 (m, 1H), 2.87 (m, 2H), 2.98 (m, 2H), 3.62 (m, 2H), 7.05–7.15 (brd, 1H), 7.24 (s, 1H), 7.34 (s, 1H), 7.46 (d, 2H), 7.94 (s, 1H), 8.20 (d, 2H).

EXAMPLES 41 to 57

Following the same method as in Example 40, the compounds shown in Table 3 were obtained.

TABLE 3

| Example No. | Compound No. | Melting point (°C.) | IR (cm$^{-1}$) | NMR Solvent; CDCl$_3$, δ value (ppm) |
|---|---|---|---|---|
| 41 | 218 | 99–101 | 1670 | 1.61(s, 6H), 2.38(s, 3H), 3.16(d, 3H), 7.18(d, 2H), 7.29(broad, 1H), 7.78(d, 2H) |
| 42 | 219 | 133–135 | 1650 | 1.62(s, 6H), 3.16(d, 3H), 3.84(s, 3H), 6.86(d, 2H), 7.31(broad, 1H), 7.90(d, 2H) |
| 43 | 224 | oil | 1677 | 1.62(s, 6H), 3.21(d, 3H), 7.54(broad, 1H), 7.69(d, 2H), 7.95(d, 2H) |
| 44 | 263 | 101–102 | 1670 | 1.62(s, 6H), 2.36(s, 3H), 3.17(d, 3H), 7.2–7.4(broad, 3H), 7.6–7.7(m, 2H) |
| 45 | 264 | 73.5–74.5 | 1675 | 1.63(s, 3H), 3.17(d, 3H), 3.80(s, 3H), 7.06(dd, 1H), 7.2–7.3(broad, 1H), 7.31(d, 1H), 7.43–7.48(m, 2H) |
| 46 | 265 | 138 | 1680 | 1.66(s, 3H), 3.20(d, 3H), 7.21(s, 1H), 7.30(s, 1H), 7.52(m, 2H), 7.6–7.9(broad, 1H), 7.88(m, 2H), 8.00(s, 1H) |
| 47 | 302 | 152.5–163.5 | 1680 | 1.39(s, 3H), 3.16(d, 3H), 7.07(s, 1H), 7.08(s, 1H), 7.32(d, 1H), 71.42(m, 2H), 7.50(m, 1H), 7.53(s, 1H), 7.7–7.9(broad, 1H) |
| 48 | 338 | 183–184 | 1665 | 0.75(t, 6H), 2.1–2.3(m, 4H), 3.22(d, 3H), 7.23(s, 1H), 7.32(s, 1H), 7.42(d, 2H), 7.93(s, 1H), 8.08(d, 2H) |
| 49 | 351 | 150–151 | 1634 | 1.80(m, 1H), 2.05(m, 1H), 2.85(m, 2H), 2.95(m, 2H), 3.10(d, 3H), 3.85(s, 3H), 6.89(d, 2H), 7.40(broad, 1H), 7.95(d, 2H) |
| 50 | 423 | 174–175 | 1663 | 1.81(m, 1H), 2.04(m, 1H), 2.86(m, 1H), 2.97(m, 2H), 3.12(d, 3H), 3.93(s, 3H), 7.06(d, 1H), 7.18(s, 1H), 7.23(s, 1H), 7.2–7.3(broad, 1H), 7.83(s, 1H), 8.03(s, 1H), 8.05(dd, 1H) |
| 51 | 435 | 165–167 | 1632 | 1.80(m, 1H), 2.05(m, 1H), 2.86(m, 2H), 2.98(m, 2H), 3.10(d, 3H), 3.90(s, 3H), 3.93(m, 3H), 6.86(d, 1H), 7.31(broad, 1H), 7.55(d, 1H), 7.64(q, 1H) |
| 52 | 436 | 123.5–124.5 | 1665 | 1.82(m, 1H), 2.06(m, 1H), 2.85(m, 2H), 3.05(m, 2H), 3.26(d, 3H), 6.37(m, 2H), 7.14(m, 2H), 7.2–7.3(broad), 1H), 7.47(t, 1H), 7.56(m, 1H), 7.82(m, 1H), 8.10(m, 1H) |
| 53 | 497 | 124–126 | 1665 | 1.16–1.32(m, 3H), 1.52–1.74(m, 3H), 1.94–2.12(m, 2H), 2.40–3.16(m, 2H), 3.16(d, 3H), 7.35–7.53(m, 4H), 7.80(d, 2H) |
| 54 | 498 | 189–191 | 1665 | 1.18(t, 3H), 1.2–1.3(broad, 4H), 1.5–1.65(broad, 2H), 1.9–2.1(m, 2H), 2.2–2.6(m, 2H), 3.70(m, 2H), 7.24(s, 1H), 7.33(s, 1H), 7.43(d, 2H), 7.93(s, 1H), 8.00(d, 2H) |
| 55 | 503 | 137–139 | 1675 | 0.84(d, 6H), 1.37–1.53(m, 3H), 1.75–1.87(m, 1H), 2.00–2.13(m, 1H), 2.77–2.89(m, 2H), 2.94–3.05(m, 2H), 3.57–3.64(m, 2H), 7.12(broad, 1H), 7.24(s, 1H), 7.33(s, 1H), 7.47(d, 2H), 7.94(s, 1H), 8.15(d, 2H) |
| 56 | 505 | amorphous | 1665 | 1.88–2.12(m, 2H), 2.60–3.40(m, 4H), 2.99(s, 3H), 3.36(m, 3H), 7.23(s, 1H), 7.32(s, 1H), 7.43(d, 2H), 7.93(s, 1H), 8.30(d, 2H) |
| 57 | 509 | 135–135.5 | 1667 | 1.75–2.0(m, 5H), 2.0–2.15(m, 1H), 2.6–3.2(broad, 4H), 3.23–3.3(broad, 2H), 3.80(t, 2H), 3.92(s, 3H), 7.05(d, 1H), 7.18(s, 1H), 7.29(s, 1H), 7.88(s, 1H), 7.19(d, 1H), 8.21(dd, 1H) |

REFERENCE EXAMPLE 2

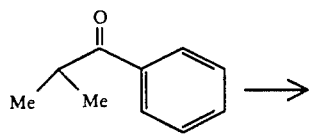

-continued

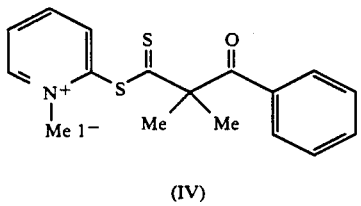

(IV)

α-Methylpropiophenone (0.75 g (5.0 mmol)) was dissolved in 15 ml of tetrahydrofuran, followed by addition of a solution of 0.61 g (5.5 mmol) of potassium t-butoxide in 15 ml of tetrahydrofuran under ice cooling for agitation for 45 minutes. To the solution was added 330 μl of carbon disulfide for agitation, under ice cooling, for 1 hour, followed by addition of 1.40 g (5.5 mmol) of 2-chloro-1-methylpyridinium iodide and 550 mg (5.5 mmol) of triethylamine, for agitation for 15 minutes, to produce the dithioester derivative (IV). Without further treatment, the reaction solution was subjected to the next reaction.

EXAMPLE 58

Synthesis of α,α-dimethyl-β-oxobenzenepropanethioamide
(Compound No. 105 of Table 1)

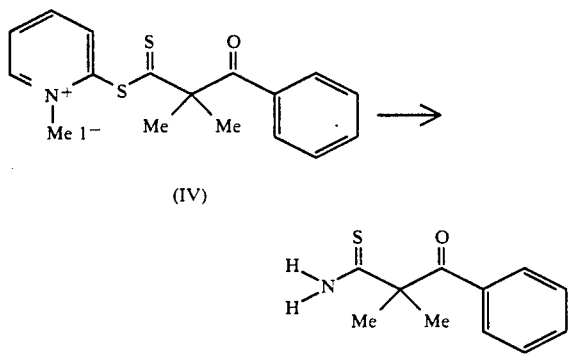

To the reaction solution produced in Reference Example 2 was added 1 ml of an aqueous 28% ammonia solution, for agitation for 4 hours. Subsequently, water was added to the reaction solution for extraction into ethyl acetate. The ethyl acetate phase was washed in water and aqueous saturated sodium chloride solution, dried over sodium sulfate for distilling off the solvent, and the resulting crude crystal was purified by silica gel column chromatography (elution solvent; ethyl acetate), to yield 160 mg of α,α-dimethyl-β-oxobenzenepropanethioamide. (Yield: 15.4%)

Melting point: 172°–175° C.

IR absorption spectrum (KBr tablet): 1664 cm⁻¹ (C=O).

NMR (solvent; CDCl₃, δ value (ppm)): 1.64 (s, 6H), 7.41 (t, 2H), 7.53 (t, 1H), 7.95 (d, 2H).

EXAMPLE 59

Following the same method as in Example 58, 4-(2-pyridyl)-α,α, N-trimethylbenzenepropanethioamide (Compound No. 258 of Table 1) was obtained. (Yield: 78.6%)

Melting point: 172°–175° C.

IR absorption spectrum (KBr tablet): 1666 cm⁻¹ (C=O).

NMR (solvent; CDCl₃, δ value (ppm)): 1.64 (s, 6H), 3.17 (d, 3H), 7.27–7.3 (broad, 1H), 7.54 (m, 2H), 7.74 (m, 2H).

EXAMPLE 60

Synthesis of 4-methoxy-N-methyl-3-nitro-β-oxo-α,α-trimethylenebenzenepropanethioamide
(Compound No. 487 of Table 1)

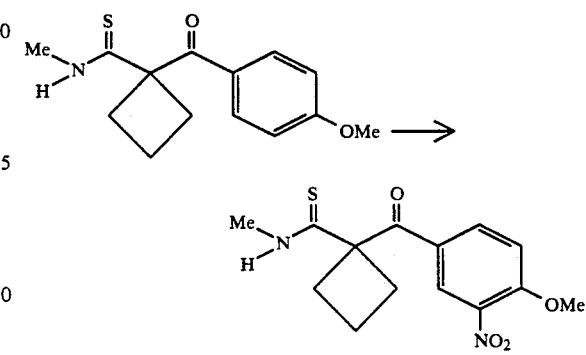

4-Methoxy-N-methyloxo-α,α-trimethylene-β-benzenepropanethioamide (560 mg (2.1 mmol)) was added to me of fuming nitric acid while keeping the reaction temperature at −40° C. or less. After the termination of the addition, agitation was further effected at the same temperature for 30 minutes. After the termination of the reaction, the reaction solution was poured into ice-cold water for extraction into chloroform. The chloroform phase was washed in water and aqueous saturated sodium chloride solution, dried over sodium sulfate for distilling off the solvent, and the resulting residue was purified by silica gel column chromatography, to produce 140 mg of 4-methoxy-N-methyl-3-nitro-β-oxo-α,α-trimethylene benzenepropane thioamide. (Yield: 21.4%)

Melting point: 145°–146° C.

IR absorption spectrum (KBr tablet): 1665 cm⁻¹ (C=O).

NMR (solvent; CDCl₃, δ value (ppm)): 1.81 (m, 1H), 2.06 (m, 1H), 2.84 (m, 2H), 2.97 (m, 2H), 3.12 (d, 3H), 4.01 (s, 3H), 7.09 (d, 2H), 7.2–7.3 (brd, 1H), 8.23 (dd, 1H), 8.52 (d, 1H).

EXAMPLES 61 to 71

Following the same method as in Example 58, the compounds shown in Table 4 were obtained.

TABLE 4

| Example No. | Compound No. | Melting point (°C.) | IR (cm⁻¹) | NMR Solvent: CDCl₃, δ value (ppm) |
|---|---|---|---|---|
| 61 | 270 | 149–151 | 1689 | 1.67(s, 6H), 3.22(d, 3H), 7.20(m, 2H), 7.50–7.65(m, 3H), 7.84(m, 1H), 8.01(m, 1H) |
| 62 | 275 | 164–165 | 1682 | 1.65(s, 6H), 2.38(s, 3H), 3.20(d, 3H), 7.02(dd, 2H), 7.30–7.55(m, 3H), 7.82(m, 1H), 7.93(m, 1H) |

TABLE 4-continued

| Example No. | Compound No. | Melting point (°C.) | IR (cm⁻¹) | NMR Solvent: CDCl₃, δ value (ppm) |
|---|---|---|---|---|
| 63 | 291 | 162 | 1672 | 1.64(s, 6H), 3.18(d, 3H), 3.92(s, 3H), 7.03(d, 1H), 7.18(d, 1H), 7.19(s, 1H), 7.35(broad, 1H), 7.79(s, 1H), 7.95(s, 1H), 8.00(dd, 1H) |
| 64 | 292 | amorphous | 1676 | 1.43(t, 3H), 1.66(s, 6H), 3.19(d, 3H), 4.16(q, 2H), 7.01(d, 1H), 7.10(s, 1H), 7.21(s, 1H), 7.77(s, 1H), 7.94(d, 1H), 8.01(dd, 1H), 8.66(broad, 1H) |
| 65 | 305 | 145–146 | 1693 | 1.27(d, 6H), 1.46(s, 6H), 2.78(m, 1H), 3.18(d, 3H), 6.79(d, 1H), 7.03(d, 1H), 7.28–7.33(m, 1H), 7.43–7.58(m, 3H), 7.80(s, 1H) |
| 66 | 337 | 192–193 | 1678 | 1.63(s, 6H), 3.14(d, 3H), 3.82(s, 6H), 3.90(s, 3H), 7.10(broad, 1H), 7.25(s, 2H) |
| 67 | 512 | amorphous | 1676 | 1.65(s, 6H), 3.19(d, 3H), 3.66(s, 3H), 7.03(d, 1H), 7.09(d, 1H), 7.19(d, 1H), 7.36(broad, 1H), 7.82(d, 1H), 8.12(dd, 1H) |
| 68 | 513 | 206 | 1676 | 1.64(s, 6H), 2.19(s, 3H), 3.18(d, 3H), 3.86(s, 3H), 6.88(s, 1H), 7.01(d, 1H), 7.02(s, 1H), 7.51(broad, 1H), 7.81(d, 1H), 8.07(dd, 1H) |
| 69 | 515 | 173.5–174 | 1680 | 1.64(s, 6H), 3.16(d, 3H), 3.25(s, 3H), 3.85(s, 3H), 4.36(s, 2H), 6.99(s, 1H), 7.01(d, 1H), 7.35(broad, 1H), 7.90(d, 1H), 8.07(dd, 1H) |
| 70 | 516 | 165-168 (decomposition) | 1684 | 1.35(t, 3H), 165(s, 6H), 3.19(d, 3H), 4.12(q, 2H), 7.00(d, 1H), 7.08(d, 1H), 7.18(d, 1H), 7.41(broad, 1H), 7.81(d, 1H), 8.09(dd, 1H) |
| 71 | 517 | 178–179 | 1676 | 1.34(t, 3H), 1.64(s, 6H), 2.21(s, 3H), 3.18(d, 3H), 4.11(q, 2H), 6.87(s, 1H), 6.99(d, 1H), 7.01(s, 1H), 7.47(broad, 1H), 7.80(d, 1H), 8.03(dd, 1H) |
| 72 | 6 | 185–187 | 1671 | 1.84(m, 1H), 2.10(m, 1H), 2.9–3.1(m, 4H), 6.85(broad, 1H), 7.24(s, 1H), 7.34(s, 1H), 7.34(broad, 1H), 7.47(d, 2H), 7.95(s, 1H), 8.14(d, 2H) |

TEST EXAMPLE 1

The aorta thoracic of a Wistar rat was resected and then suspended in a Klebs-Heneleit solution kept at 37° C., according to the Weir and Weston's method (Br. J. Pharmac., 88, 121, (1986)), to determine the dose (IC30 20 mMK) of a drug suppressing 30% of 20 mMK shrinkage. As control, the same test was done about the known compound A described in Bull. Soc. Chem. Fr., 1975, 829.

TABLE 5

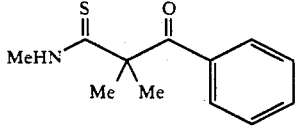

Compound A

| Compound No. in Table 1 | Rat aorta IC30 20 mMK (μM) |
|---|---|
| 224 | 5.0 |
| 226 | 13.0 |
| 265 | 0.62 |
| 356 | 2.1 |
| 357 | 0.18 |
| Compound A | 13.6 |

TEST EXAMPLE 2

At a dose of 3 mg/kg or 10 mg/kg, the compound of the present invention was orally administered to spontaneous hypertensive rats (OKAMOTO-AOKI strain) with an average blood pressure of 150 mmHg or more. According to the direct method described by Nakano H. and Takayanagi K., Japanese Journal of Pharmacology, Vol. 25, 25 (1975), blood pressure and cardiac output were measured. Using the compound A used in the Test Example 1 as control, the same test was done.

The results 2 hours after the dosing are shown in Table 6.

TABLE 6

| Compound No. in Table 1 | Dose (mg/kg) | Mean blood pressure (mm Hg) | |
|---|---|---|---|
| | | Value prior to dosing | Blood pressure decrease |
| 224 | 10 | 177.5 | 38.8 |
| 226 | 10 | 177.3 | 35.9 |
| 265 | 3 | 163.1 | 76.5 |
| 302 | 10 | 176.1 | 51.9 |
| 342 | 10 | 167.3 | 31.2 |
| 356 | 10 | 172.0 | 58.9 |
| 357 | 10 | 158.4 | 78.4 |
| Compound A | 10 | 180.3 | 14.1 |

What is claimed is:

1. A β-oxo-β-benzenepropanethioamide derivative of the formula:

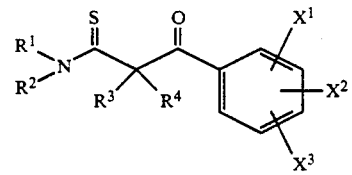

wherein $R^1$ and $R^2$ independently represent hydrogen, alkyl or 1-6 carbon atoms or cycloalkyl of 3-6 carbon atoms, or $R^1$ and $R^2$ taken together represent alkylene of 3-6 carbon atoms; $R^3$ represents hydrogen, alkyl of 1-6 carbon atoms or cycloalkyl of 3-6 carbon atoms; $R^4$ represents alkyl of 1-6 carbon atoms or cycloalkyl of 3-6 carbon atoms; or $R^3$ and $R^4$ taken together represent alkylene of 2-5 carbon atoms; $X^1$, $X^2$ and $X^3$ independently represent hydrogen, halogen, alkyl of 1-6 carbon atoms, cycloalkyl of 3-6 carbon atoms, alkoxy of 1-6 carbon atoms, trifluoromethyl, cyano, nitro, dialkylamino of 2-12 carbon atoms, sulfamoyl or a five-membered or six-membered heterocyclic group containing 1-3 nitrogen atoms as the heteroatom, which group is unsubstituted or is substituted by alkyl of 1-6 carbon atoms, alkoxy of 1-6 carbon atoms, halogen, cyano, phenyl, alkylthio of 1-6 carbon atoms or haloalkyl of -6 carbon atoms, except for the case where $R^1$ represents hydrogen, $R^2$ represents n-propyl, $R^3$ represents hydrogen, $R^4$ represents methyl and $X^1$, $X^2$ and $X^3$ represent hydrogen; and the case where $R^1$ represents hydrogen, $R^2$, $R^3$ and $R^4$ represent methyl, and $X^1$, $X^2$ and $X^3$ represent hydrogen, or a pharmaceutically acceptable acid addition salt thereof.

2. A compound as claimed in claim 1, wherein at least one of $X^1$, $X^2$ and $X^3$ represents halogen, alkyl of 1-6 carbon atoms, cycloalkyl of 3-6 carbon atoms, alkoxy of 1-6 carbon atoms, trifluoromethyl, cyano, nitro, dialkylamino of 2-12 carbon atoms, sulfamoyl or a five-membered or six-membered heterocyclic group containing 1-3 nitrogen atoms as the hetero atom, which group is unsubstituted or is substituted by alkyl of 1-6 carbon atoms, alkoxy of 1-6 carbon atoms, halogen, cyano, phenyl, alkylthio of 1-6 carbon atoms or haloalkyl of 1-6 carbon atoms.

3. A compound as claimed in claim 1, wherein at least one of $X^1$, $X^2$ and $X^3$ represents a five-membered or six-membered heterocyclic group containing 1-3 nitrogen atoms as the hetero atom, which group is unsubstituted or is substituted by alkyl of 1-6 carbon atoms, alkoxy of 1-6 carbon atoms, halogen, cyano, phenyl, alkylthio of 1-6 carbon atoms or haloalkyl of 1-6 carbon atoms.

4. A compound as claimed in claim 3, wherein the five-membered or six-membered heterocyclic group is selected from the group consisting of pyrrolyl, imidazolyl, pyrazolyl, triazolyl, thiazolyl, oxoazolyl, pyridyl, pyridazinyl, pyridazinonyl, pyrrolidionyl, pyridonyl and pyrimidinyl.

5. A compound as claimed in claim 4, wherein the five-membered or six-membered heterocyclic group is selected from the group consisting of pyrrolyl, imidazolyl, triazolyl, pyridyl and pyridonyl.

6. A compound as claimed in claim 5, wherein the five-membered or six-membered heterocyclic group is imidazolyl.

7. A compound as claimed in claim 3, wherein the substituent is selected from the group consisting of alkyl of 1-6 carbon atoms, halogen, phenyl and alkylthio of 1-6 carbon atoms.

8. A compound as claimed in claim 7, wherein the substituent is halogen.

9. A pharmaceutical composition containing a pharmaceutically effective amount of a compound as claimed in claim 1 and a pharmaceutically acceptable carrier.

10. A pharmaceutical composition for potassium channel opening, containing an effective amount of a compound as claimed in claim 1 and a pharmaceutically acceptable carrier.

* * * * *